(12) United States Patent
O'Brien et al.

(10) Patent No.: US 7,574,792 B2
(45) Date of Patent: Aug. 18, 2009

(54) METHOD OF MANUFACTURING AN IMPLANTABLE WIRELESS SENSOR

(75) Inventors: David O'Brien, Norcross, GA (US); Jason White, Atlanta, GA (US); Michael Fonseca, Atlanta, GA (US); Jason Kroh, Villa Rica, GA (US); Mark Allen, Atlanta, GA (US); David Stern, Grayson, GA (US)

(73) Assignee: CardioMEMS, Inc., Atlanta, GA (US)

( * ) Notice: Subject to any disclaimer, the term of this patent is extended or adjusted under 35 U.S.C. 154(b) by 81 days.

(21) Appl. No.: 11/472,905

(22) Filed: Jun. 22, 2006

(65) Prior Publication Data

US 2006/0235310 A1 Oct. 19, 2006

Related U.S. Application Data

(62) Division of application No. 10/943,772, filed on Sep. 16, 2004, now abandoned.

(60) Provisional application No. 60/503,745, filed on Sep. 16, 2003.

(51) Int. Cl.
*H01F 7/06* (2006.01)

(52) U.S. Cl. .............................. 29/606; 29/600; 29/604; 29/605

(58) Field of Classification Search ................... 29/606, 29/600, 605, 604, 613, 831, 832, 835; 600/486, 600/300, 377, 301, 422, 481, 423, 485; 324/488, 324/546, 600, 601; 342/488, 456, 600, 601
See application file for complete search history.

(56) References Cited

U.S. PATENT DOCUMENTS

| | | |
|---|---|---|
| 2,769,863 A | 6/1957 | Von Wittern |
| 3,419,834 A | 12/1968 | McKechnie |
| 3,867,950 A | 2/1975 | Fischell |
| 3,942,382 A | 3/1976 | Hok |
| 3,958,558 A | 5/1976 | Dunphy et al. |
| 4,026,276 A | 5/1977 | Chubbuck |

(Continued)

FOREIGN PATENT DOCUMENTS

CA 1158061 6/1983

(Continued)

OTHER PUBLICATIONS

Adams, Jr., K. F. "Guiding Heart Failure Care by Invasive Hemodynamic Measurements: Possible Or Useful?", *Journal of Cardiac Failure* Apr. 2002, vol. 8, No. 2, 71-73.

(Continued)

*Primary Examiner*—Minh Trinh
*Assistant Examiner*—Tai Nguyen
(74) *Attorney, Agent, or Firm*—Kilpatrick Stockton LLP

(57) ABSTRACT

In the disclosed method of manufacturing an implantable wireless sensor, a cavity is etched in one side of a first substrate. A conductive structure are formed on the base of the cavity. A second conductive structureare formed on a surface of a second substrate, and the two substrates are mutually imposed such that the two conductive plates and coils are disposed in opposed, spaced-apart relation. A laser is then used to cut away perimeter portions of the imposed substrates and simultaneously to heat bond the two substrates together such that the cavity in the first substrate is hermetically sealed.

40 Claims, 19 Drawing Sheets

U.S. PATENT DOCUMENTS

| | | | |
|---|---|---|---|
| 4,127,110 A | 11/1978 | Bullara | |
| 4,206,762 A | 6/1980 | Cosman | |
| 4,207,903 A | 6/1980 | O'Neil | |
| RE30,366 E | 8/1980 | Rasor | |
| 4,237,900 A | 12/1980 | Schulman et al. | |
| 4,354,506 A | 10/1982 | Sakaguchi et al. | |
| 4,378,809 A | 4/1983 | Cosman | |
| 4,485,813 A | 12/1984 | Anderson et al. | |
| 4,494,950 A | 1/1985 | Fischell | |
| 4,521,684 A | 6/1985 | Gilby et al. | |
| 4,596,563 A | 6/1986 | Pande | |
| 4,713,540 A | 12/1987 | Gilby et al. | |
| 4,718,425 A | 1/1988 | Tanaka et al. | |
| 4,796,641 A | 1/1989 | Mills et al. | |
| 4,815,472 A | 3/1989 | Wise et al. | |
| 4,833,920 A | 5/1989 | Knecht et al. | |
| 4,846,191 A | 7/1989 | Brockway et al. | |
| 4,890,623 A | 1/1990 | Cook et al. | |
| 4,899,752 A | 2/1990 | Cohen | |
| 4,905,575 A | 3/1990 | Knecht et al. | |
| 4,913,147 A | 4/1990 | Fahlstrom et al. | |
| 4,934,369 A | 6/1990 | Maxwell | |
| 4,987,897 A | 1/1991 | Funke | |
| 5,113,868 A | 5/1992 | Wise et al. | |
| 5,115,128 A | 5/1992 | Cook | |
| 5,129,394 A | 7/1992 | Mehra | |
| 5,165,289 A | 11/1992 | Tilmans | |
| 5,181,423 A | 1/1993 | Philipps et al. | |
| 5,192,314 A | 3/1993 | Daskalakis | |
| 5,207,103 A | 5/1993 | Wise et al. | |
| 5,265,606 A | 11/1993 | Kujawski | |
| 5,312,674 A * | 5/1994 | Haertling et al. | 428/210 |
| 5,331,453 A | 7/1994 | Lipskey | |
| 5,353,800 A | 10/1994 | Pohndorf et al. | |
| 5,373,852 A | 12/1994 | Harrison et al. | |
| 5,411,551 A | 5/1995 | Winston et al. | |
| 5,431,171 A | 7/1995 | Harrison et al. | |
| 5,440,300 A | 8/1995 | Spillman, Jr. | |
| 5,487,760 A | 1/1996 | Villafana | |
| 5,497,099 A | 3/1996 | Walton | |
| 5,515,041 A | 5/1996 | Spillman, Jr. | |
| 5,535,752 A | 7/1996 | Halperin et al. | |
| 5,538,005 A | 7/1996 | Harrison et al. | |
| 5,551,427 A | 9/1996 | Altman | |
| 5,566,676 A | 10/1996 | Rosenfeldt et al. | |
| 5,593,430 A | 1/1997 | Renger | |
| 5,600,245 A | 2/1997 | Yamamoto et al. | |
| 5,626,630 A | 5/1997 | Markowitz et al. | |
| 5,686,841 A | 11/1997 | Stolarczyk et al. | |
| 5,695,155 A | 12/1997 | Macdonald et al. | |
| 5,702,427 A | 12/1997 | Ecker et al. | |
| 5,703,576 A | 12/1997 | Spillman, Jr. et al. | |
| 5,713,917 A | 2/1998 | Leonhardt et al. | |
| 5,722,414 A | 3/1998 | Archibald et al. | |
| 5,723,791 A | 3/1998 | Koch et al. | |
| 5,743,267 A | 4/1998 | Nikolic et al. | |
| 5,796,827 A | 8/1998 | Coppersmith et al. | |
| 5,807,265 A | 9/1998 | Itoigawa et al. | |
| 5,836,886 A | 11/1998 | Itoigawa et al. | |
| 5,860,938 A | 1/1999 | Lafontaine et al. | |
| 5,899,927 A | 5/1999 | Ecker et al. | |
| 5,935,084 A | 8/1999 | Southworth | |
| 5,942,991 A | 8/1999 | Gaudreau et al. | |
| 5,967,986 A | 10/1999 | Cimochowski et al. | |
| 6,015,386 A | 1/2000 | Kensey et al. | |
| 6,015,387 A | 1/2000 | Schwartz et al. | |
| 6,019,729 A | 2/2000 | Itoigawa et al. | |
| 6,024,704 A | 2/2000 | Meador et al. | |
| 6,025,725 A | 2/2000 | Gershenfeld et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Geierbach | |
| 6,111,520 A * | 8/2000 | Allen et al. | 340/870.16 |
| 6,113,553 A | 9/2000 | Chubbuck | |
| 6,134,461 A | 10/2000 | Say et al. | |
| 6,140,740 A | 10/2000 | Porat et al. | |
| 6,159,156 A | 12/2000 | Van Bockel | |
| 6,198,965 B1 | 3/2001 | Penner et al. | |
| 6,201,980 B1 | 3/2001 | Darrow et al. | |
| 6,206,835 B1 | 3/2001 | Spillman, Jr. et al. | |
| 6,237,398 B1 | 5/2001 | Porat et al. | |
| 6,239,724 B1 | 5/2001 | Doron et al. | |
| 6,277,078 B1 | 8/2001 | Porat et al. | |
| 6,278,379 B1 * | 8/2001 | Allen et al. | 340/870.16 |
| 6,287,253 B1 | 9/2001 | Ortega et al. | |
| 6,373,264 B1 | 4/2002 | Matsumoto et al. | |
| 6,409,674 B1 | 6/2002 | Brockway et al. | |
| 6,442,413 B1 | 8/2002 | Silver | |
| 6,454,720 B1 | 9/2002 | Clerc et al. | |
| 6,495,895 B1 * | 12/2002 | Peterson et al. | 257/434 |
| 6,548,176 B1 | 4/2003 | Gwo | |
| 6,645,143 B2 | 11/2003 | Van Tessel et al. | |
| 6,667,725 B1 | 12/2003 | Simmons et al. | |
| 6,682,490 B2 | 1/2004 | Roy et al. | |
| 6,765,493 B2 | 7/2004 | Lonsdale et al. | |
| 6,890,300 B2 | 5/2005 | Lloyd et al. | |
| 6,923,769 B2 | 8/2005 | Nishii et al. | |
| 6,926,670 B2 | 8/2005 | Rich et al. | |
| 6,939,299 B1 | 9/2005 | Petersen et al. | |
| 7,060,038 B2 | 6/2006 | Letort et al. | |
| 2002/0115920 A1 | 8/2002 | Rich et al. | |
| 2002/0138009 A1 | 9/2002 | Brockway et al. | |
| 2002/0151816 A1 | 10/2002 | Rich et al. | |
| 2002/0188207 A1 | 12/2002 | Richter | |
| 2003/0010808 A1 | 1/2003 | Uhland et al. | |
| 2003/0031587 A1 | 2/2003 | Hu et al. | |
| 2003/0136417 A1 | 7/2003 | Fonseca et al. | |
| 2003/0139677 A1 | 7/2003 | Fonseca et al. | |
| 2004/0011650 A1 | 1/2004 | Zenhausern et al. | |
| 2004/0057589 A1 | 3/2004 | Pedersen et al. | |
| 2004/0122494 A1 | 6/2004 | Eggers et al. | |
| 2005/0075697 A1 | 4/2005 | Olson et al. | |
| 2005/0085703 A1 | 4/2005 | Behm | |
| 2005/0154321 A1 | 7/2005 | Wolinsky et al. | |
| 2005/0187482 A1 | 8/2005 | O'Brien et al. | |

FOREIGN PATENT DOCUMENTS

| | | |
|---|---|---|
| DE | 19644858.5 | 10/1996 |
| EP | 0337035 | 11/1993 |
| EP | 0646365 | 4/1995 |
| WO | WO-83/03348 | 10/1983 |
| WO | WO 90/06723 | 6/1990 |
| WO | WO 95/33517 | 12/1995 |
| WO | WO 97/09926 | 3/1997 |
| WO | WO 97/32518 | 9/1997 |
| WO | WO 97/32519 | 9/1997 |
| WO | WO 97/33513 | 9/1997 |
| WO | WO 99/34731 | 7/1999 |
| WO | WO 00/16686 | 3/2000 |
| WO | WO 01/00089 | 1/2001 |
| WO | WO 01/87137 | 11/2001 |
| WO | WO 01/97908 | 12/2001 |
| WO | WO 03/061504 | 7/2003 |

OTHER PUBLICATIONS

Akin, T. et al., "RF Telemetry Powering and Controlling of Hermetically Sealed Integrated Sensors and Actuators", *Center for Integrated Sensors and Circuits*, 145-148, ; Department of Electrical Engineering and Computer Science; University of Michigan; Ann Arbor, Michigan 48109-2122.

Akingba, G. et al., "An Implantable Pressure Sensor for Aneurysmal Disease".

Baum, R. A. et al., "Aneurysm Sac Pressure Measurements After Endovascular Repair of Abdominal Aortic Aneurysms", *Journal of Vascular Surgery* Jan. 2001, vol. 33, No. 1, 32-41.

Chuter, T. et al., "Endovascular and Surgical Techniques", *Eur J. Vasc Endovasc Surg* Jan. 1997, vol. 13, 85-87.

Collins, "Miniature Passive Pressure Transensor for Implanting in the Eye", *IEEE Transactions on Biomedical Engineering* Apr. 1967.

Dehennis, A. et al., "A Double-Sided Single-Chip Wireless Pressure Sensor", *Engineering Research Center for Wireless Integrated Microsystems; Department of Electrical Engineering and Computer Science; The University of Michigan, Ann Arbor, MI 48109-2122 US.*

Dehennis, A. et al., "A Passive-Telemetry-Based Pressure Sensing System", *NSF Engineering Research Center for Wireless Integrated Microsystems; Department of Electrical Engineering and Computer Science; The University of Michigan, Ann Arbor, MI 48109-2122 US.*

Farrar, J. T. et al., "Telemetering of Intraenteric Pressure In Man By An Externally Energized Wireless Capsule", *Science* Jun. 17, 1960, New Series, vol. 131, Issue 3416, 1814.

Gawenda, M. et al., "Intra-Aneurysm Sac Pressure-The Holy Gail of Endoluminal Grafting of AAA", *Eur J Vasc Endovasc Surg* Aug. 2002, vol. 24, 139-145.

Gawenda, M. et al., "Pressure if Transmitted Through PTFE and Dacron Grafts Leading the Aneurysm Sac Pressure Endoluminal Grafting of AAA - An In Vitro Study", *Vascular Centre, University of Cologne, Germany.*

George, et al., "Ceramics Windows to the Future", http://matse1.mse.uiuc.edu/ceramics/ceramics.html 1995, 4.

Harris, P. L. et al., "Predicting Failure of Endovascular Anerurysm Repair", *Eur J Vas Endovasc Surg* Jan. 1999, vol. 17, 1-2.

Haynes, H. E. et al., "Medical Electronics: The Pill That Talks", *DEP, Camden, N.J.*.

Magalski, A. et al., "Continuous Ambulatory Right Heart Pressure Measurements With an Implantable Hemodynamic Monitor: A Multicenter, 12-Month Follow-Up Study of Patients With Chronic Heart Failure", *Journal of Cardiac Failure* Apr. 2002, vol. 8, 63-70.

Manwaring, M. L. et al., "Remote Monitoring of Intercranial Pressure", *Institute of Concology; Annals of the Academy of Studencia* Apr. 2001, 77-80.

Ouriel, K. "Role of Intrasac Pressure Measurements After EVAR: Can They Be Followed Noninvasively?", *Combined Session: Vascular Surgery and Interventional Radiology*, VII 4.1.

Parodi, J. C. et al., "Intra-Eneurysmal Pressure After Incomplete Endovascular Exclusion", *Journal of Vascular Surgery* Nov. 2001, vol. 24, No. 5, 909-914.

Schurink, GWH et al., "Endoleakage After Stent-Graft Treatment of Abdominal Aneurysm: Implications On Pressure and Imaging-An In Vitro Study", *Journal of Vascular Surgery*, vol. 28, No. 2, 234-241.

Schurink, GWH et al., "Experimental Study of the Influence of Endoleakage Size on Pressure in the Aneurysm Sac and the Consequences of Thrombosis", *British Journal of Surgery* 2002, 87:71-78.

Shabetai, R. "Monitoring Heart Failure Hemodynamics With an Implanted Device: Its Potential to Improve Outcome", *Journal of the American College of Cardiology* Feb. 19, 2003, vol. 41, No. 4, 572-573.

Skillern, C. S. et al., "Endotension In An Experimental Aneurysm Model", *Journal of Vascular Surgery* Oct. 2002, vol. 36, No. 4, 814-817.

Sonesson, B. et al., "Intra-Aneurysm Pressure Measurements in Successfully Excluded Abdominal Aortic Aneurysm After Endovascular Repair in the Absence of Graft-Related Endoleak", *Journal of Vascular Surgery* Apr. 2003, vol. 37, 773-738.

Treharne, G. D. et al., "Quality Control During Endovascular Aneurysm Repair: Monitoring Aneurysmal Sac Pressure and Superficial Femoral Artery Flow Velocity", *J. Endovasc Surg.* 1999, 6:239-245.

Vallabhane, S. R. et al., "Aortic Side Branch Perfusion Alone Does Not Account for High Intra-Sac Pressure After Endovascular Repair (EVAR) in the Absence of Graft-Related Endoleak", *Royal Liverpool University Hospital, Liverpool, UK.*

Zhe, J. et al., "A MEMS Device for Measurement of Skin Friction With Capacitive Sensing", *Department of Mechanical Engineering, Columbia University, NY 10027; Microelectronics Research Center, New Jersey Institute of Technology, Newark, NJ 07102.*

\* cited by examiner

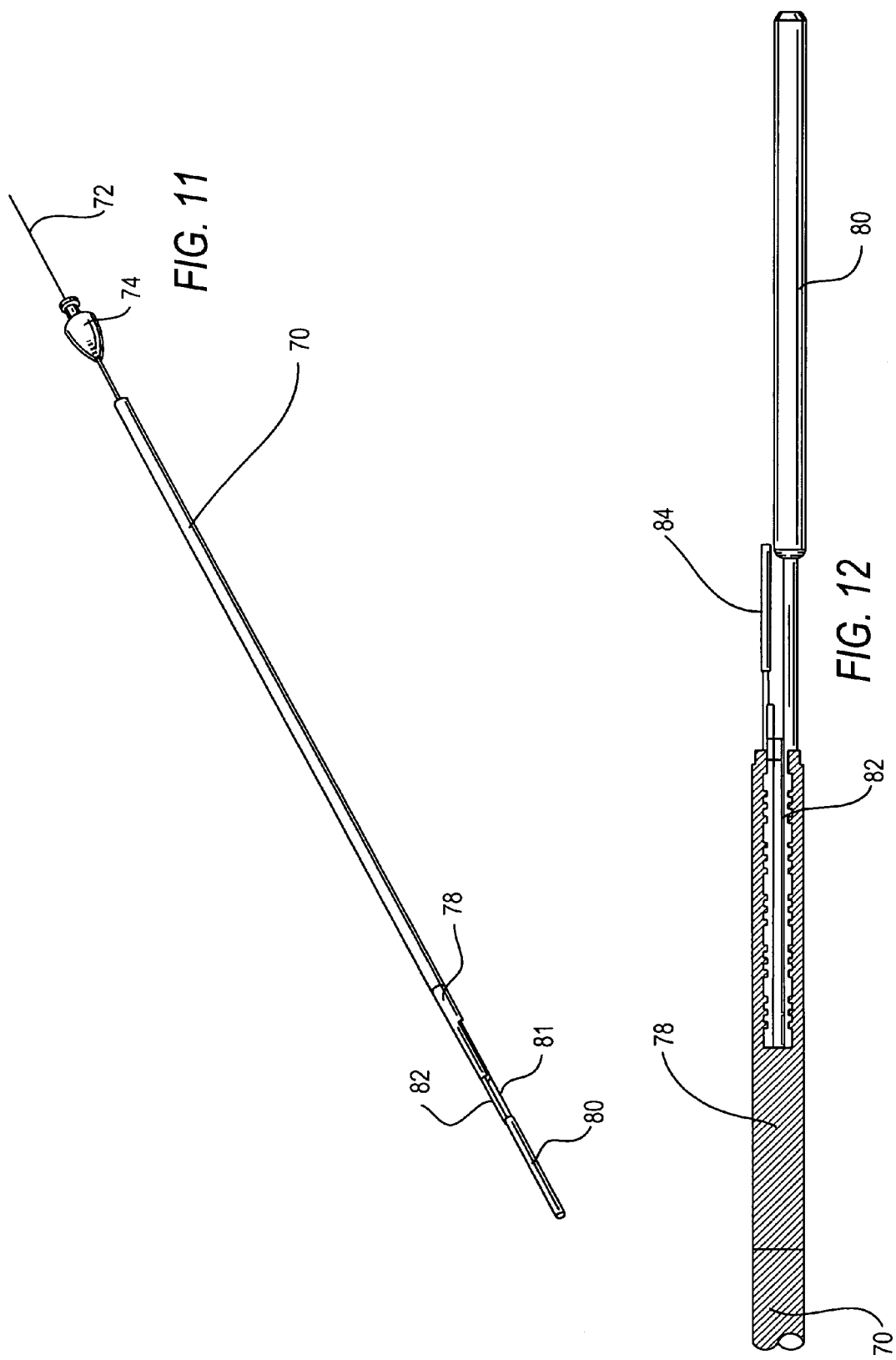

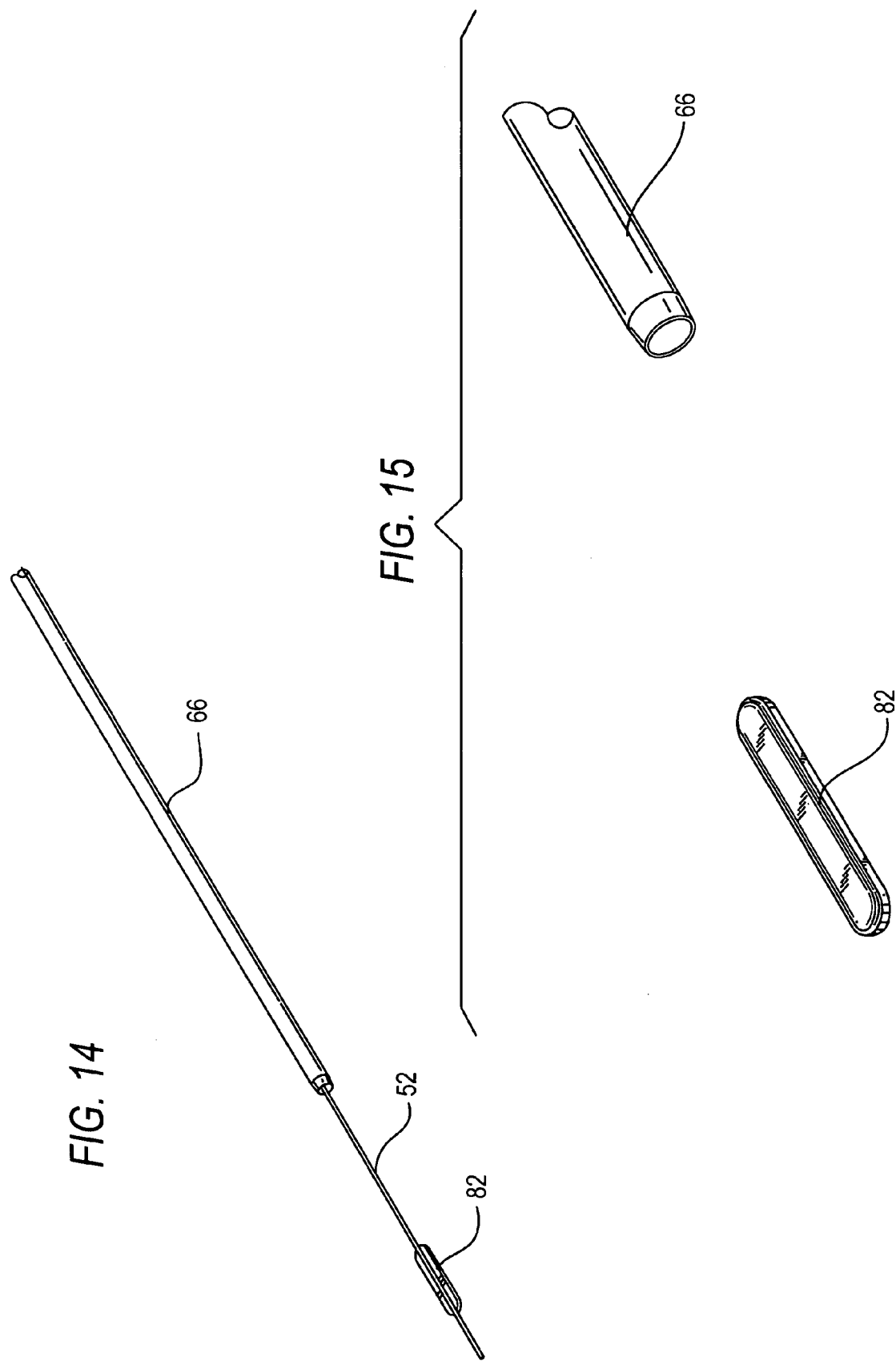

METHOD OF MANUFACTURING AN IMPLANTABLE WIRELESS SENSOR

CROSS-REFERENCE TO RELATED APPLICATION

This application is a divisional application of U.S. patent application Ser. No. 10/943,772, filed Sep. 16, 2004 now abandoned, which is based upon co-pending, commonly assigned U.S. provisional patent application Ser. No. 60/503,745, filed Sep. 16, 2003, incorporated herein by reference in its entirety.

FIELD OF THE INVENTION

The application is directed to an implantable wireless sensor. More particularly, this invention is directed to a wireless, unpowered, micromechanical sensor that can be delivered using endovascular techniques, to measure a corporeal parameter such as pressure or temperature.

BACKGROUND OF THE INVENTION

Abdominal aortic aneurysms represent a dilatation and weakening of the abdominal aorta which can lead to aortic rupture and sudden death. Previously, the medical treatment of abdominal aortic aneurysms required complicated surgery with an associated high risk of injury to the patient. More recently, endografts (combining stents and grafts into a single device) have been developed that can be inserted through small incisions in the groin. Once in place, these endografts seal off the weakened section of the aorta. The aneurysms can then heal, eliminating the risk of sudden rupture. This less invasive form of treatment for abdominal aortic aneurysms has rapidly become the standard of care for this disease. An example of an endograft device is disclosed in Kornberg, U.S. Pat. No. 4,617,932.

A significant problem with endografts is that, due to inadequate sealing of the graft with the aorta, leaks can develop that allow blood to continue to fill the aneurysmal sac. Left undiscovered, the sac will continue to expand and potentially rupture. To address this situation, patients who have received endograft treatment for their abdominal aortic aneurysms are subjected to complex procedures that rely on injection of contrast agents to visualize the interior of the aneurysm sac. These procedures are expensive, not sensitive, and painful. In addition, they subject the patient to additional risk of injury. See, for example, Baum R A et al., "Aneurysm sac pressure measurements after endovascular repair of abdominal aortic aneurysms", *The Journal of Vascular Surgery*, January 2001, and Schurink G W et al., "Endoleakage after stent-graft treatment of abdominal aneurysm: implications on pressure and imaging—an in vitro study", *The Journal of Vascular Surgery*, August 1998. These articles provide further confirmation of the problem of endograft leakage and the value of intra-sac pressure measurements for monitoring of this condition.

Thus, there is a need for a method of monitor the pressure within an aneurysm sac that has undergone repair by implantation of an endograft to be able to identify the potential presence of endoleaks. Furthermore, this method should be accurate, reliable, safe, simple to use, inexpensive to manufacture, convenient to implant and comfortable to the patient.

An ideal method of accomplishing all of the above objectives would be to place a device capable of measuring pressure within the aneurysm sac at the time of endograft insertion. By utilizing an external device to display the pressure being measured by the sensor, the physician will obtain an immediate assessment of the success of the endograft at time of the procedure, and outpatient follow-up visits will allow simple monitoring of the success of the endograft implantation.

An example of an implantable pressure sensor designed to monitor pressure increases within an aneurysmal sac is shown in Van Bockel, U.S. Pat. No. 6,159,156. While some of the above objectives are accomplished, this device has multiple problems that would make its use impractical. For example, the sensor system disclosed in the Van Bockel patent relies on a mechanical sensing element that cannot be practically manufactured in dimensions that would allow for endovascular introduction. In addition, this type of pressure sensor would be subject to many problems in use that would limit its accuracy, stability and reliability. One example would be the interconnection of transponder and sensor as taught by Van Bockel, such interconnection being exposed to body fluids which could disrupt its function. This would impact the device's ability to maintain accurate pressure reading over long periods of time. A fundamental problem with sensors is their tendency to drift over time. A sensor described in the Van Bockel patent would be subject to drift as a result of its failure to seal the pressure sensing circuit from the external environment. Also, by failing to take advantage of specific approaches to electronic component fabrication, allowing for extensive miniaturization, the Van Bockel device requires a complex system for acquiring data from the sensor necessary for the physician to make an accurate determination of intra-aneurysmal pressure.

OBJECTS OF THE INVENTION

It is an object of this invention to provide an implantable wireless sensor.

It is also an object of this invention to provide a wireless, unpowered, micromechanical sensor that can be delivered endovascularly.

It is a further object of this invention to provide an implantable, wireless, unpowered sensor that can be delivered endovascularly to measure pressure and/or temperature.

It is a yet further object of this invention to provide a method of preparing a micromechanical implantable sensor.

It is a yet further object of this invention to provide a micromechanical sensor with a hermetically sealed, unbreached pressure reference for enhanced stability.

These and other objects of the invention will become more apparent from the discussion below.

SUMMARY OF THE INVENTION

The present invention comprises a method for manufacturing a device that can be implanted into the human body using non-surgical techniques to measure a corporeal parameter such as pressure, temperature, or both. Specific target locations could include the interior of an abdominal aneurysm or a chamber of the heart. This sensor is fabricated using MicroElectroMechanical Systems (MEMS) technology, which allows the creation of a device that is small, accurate, precise, durable, robust, biocompatible, radiopaque and insensitive to changes in body chemistry, biology or external pressure. This device will not require the use of wires to relay pressure information externally nor need an internal power supply to perform its function.

Stated somewhat more specifically, according to the disclosed method, a cavity is etched in one side of a first substrate. A conductive central plate and surrounding conductive coil is formed on the base of the cavity. A second conductive central plate and surrounding conductive coil is formed on a surface of a second substrate, and the two substrates are mutually imposed such that the two conductive plates and coils are disposed in opposed, spaced-apart relation. A laser is then used to cut away perimeter portions of the imposed substrates and simultaneously to heat bond the two substrates together such that the cavity in the first substrate is hermetically sealed.

According to one embodiment of the invention, the second conductive plate and coil are formed on the upper surface of the second substrate. According to another embodiment, the second substrate has a cavity etched into its upper side, and the conductive plate and coil are formed on the base of the cavity. According to this second embodiment, when the two substrates are mutually imposed, the cavities in the respective substrates communicate to form a hollow. The subsequent laser operation hermetically seals the hollow within the sensor body.

BRIEF DESCRIPTION OF THE DRAWINGS

FIGS. 9 to 12 show additional details of the tethering system;

FIGS. 13 to 15 show details of the delivery system;

DETAILED DESCRIPTION OF THE INVENTION

Figure 1:
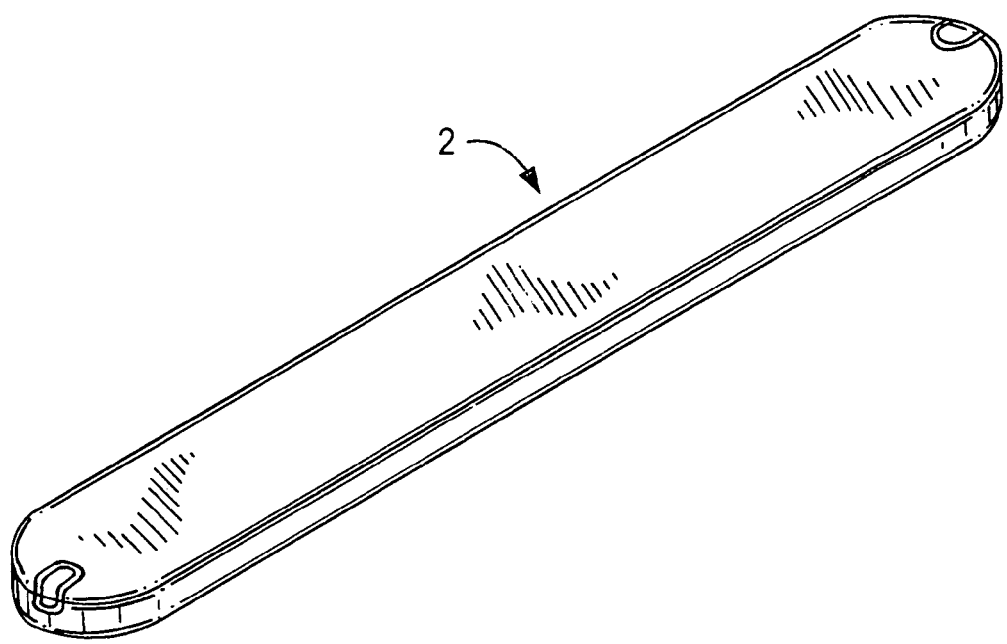
FIG. 1 is an oblique perspective view of an embodiment of the invention.

The invention can perhaps be better understood by referring to the drawings. FIG. 1 is an oblique, perspective view of a sensor 2, an embodiment of the invention. Sensor 2 preferably has an outer coating of biocompatible silicone.

Figure 2:
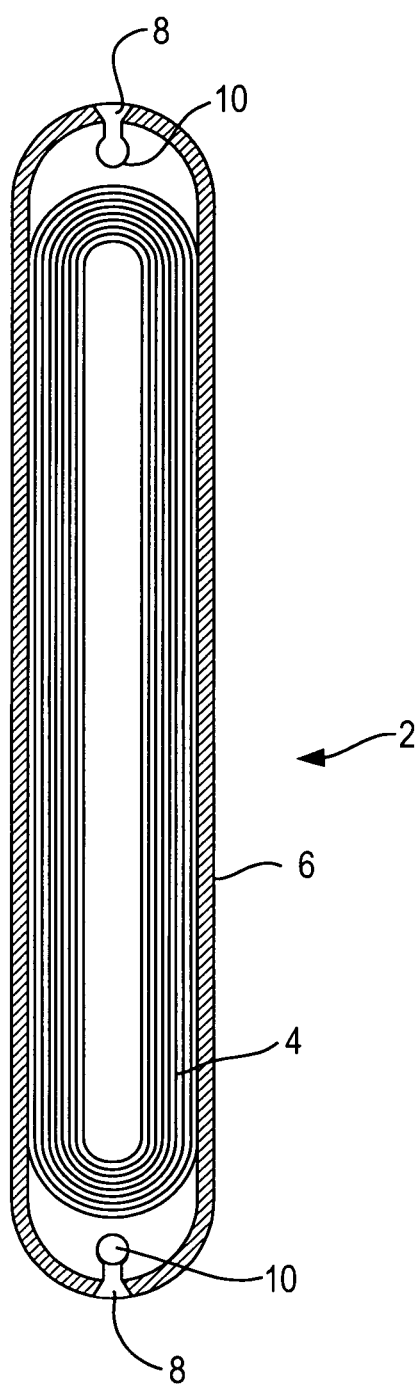
FIG. 2 is a top, partly cross-sectional view of the embodiment of the invention shown in FIG. 1.

FIG. 2 is a top, partial cross-section of a schematic representation of sensor 2 where a wire spiral inductor coil 4 is positioned in planar fashion in a substrate 6. Optionally sensor 2 may have recesses 8, each with a hole 10, to receive a tether wire (not shown here) for delivery of the device into a human patient, as described below.

Figure 3:
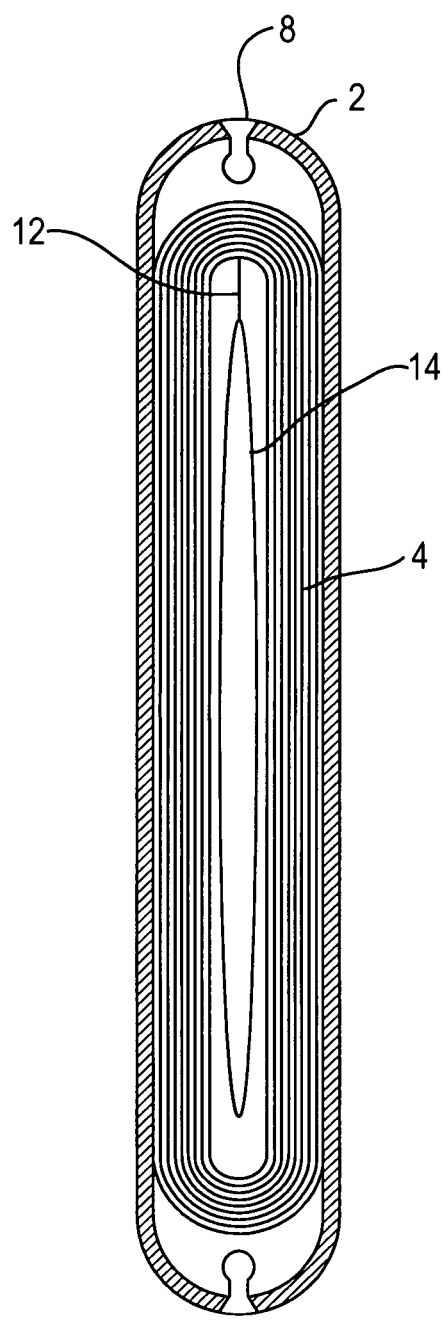
FIG. 3 is a top, partly cross-sectional view of another embodiment of the invention.

In the embodiment of the invention shown in FIG. 3, a wire 12 connects coil 4 to a capacitor plate 14 positioned within coil 4.

Figure 4:
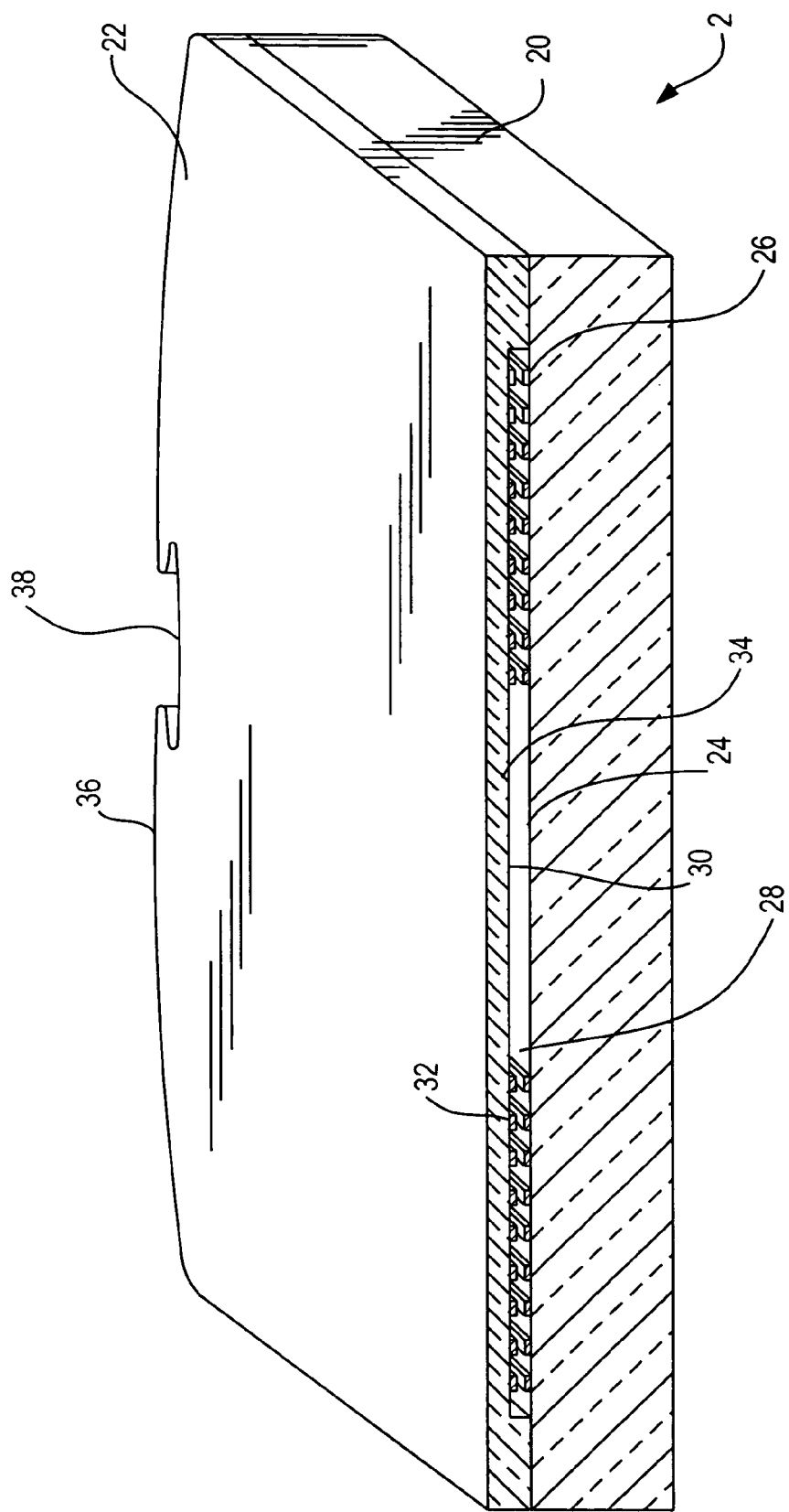
FIG. 4 is an oblique, cross-sectional view of the embodiment of the invention shown in FIG. 2.

FIG. 4 is a slightly oblique cross-section across its width of the embodiment of the invention shown in FIG. 2, where it can be seen that sensor 2 is comprised of a lower substrate 20 and an upper substrate 22. Lower substrate 20 and upper substrate 22 are constructed from a suitable material, such as glass, fused silica, sapphire, quartz, or silicon. Fused silica is the preferred material of construction. Lower substrate 20 has on its upper surface 24 an induction coil 26, and upper substrate 22 has a recess 28 with a surface 30 having an induction coil 32 thereon. The top surface of upper substrate 22 forms a membrane 34 capable of mechanically responding to changes in a patient's physical property, such as pressure. The end 36 of sensor 2 has a notch or recess 38.

Figure 5:
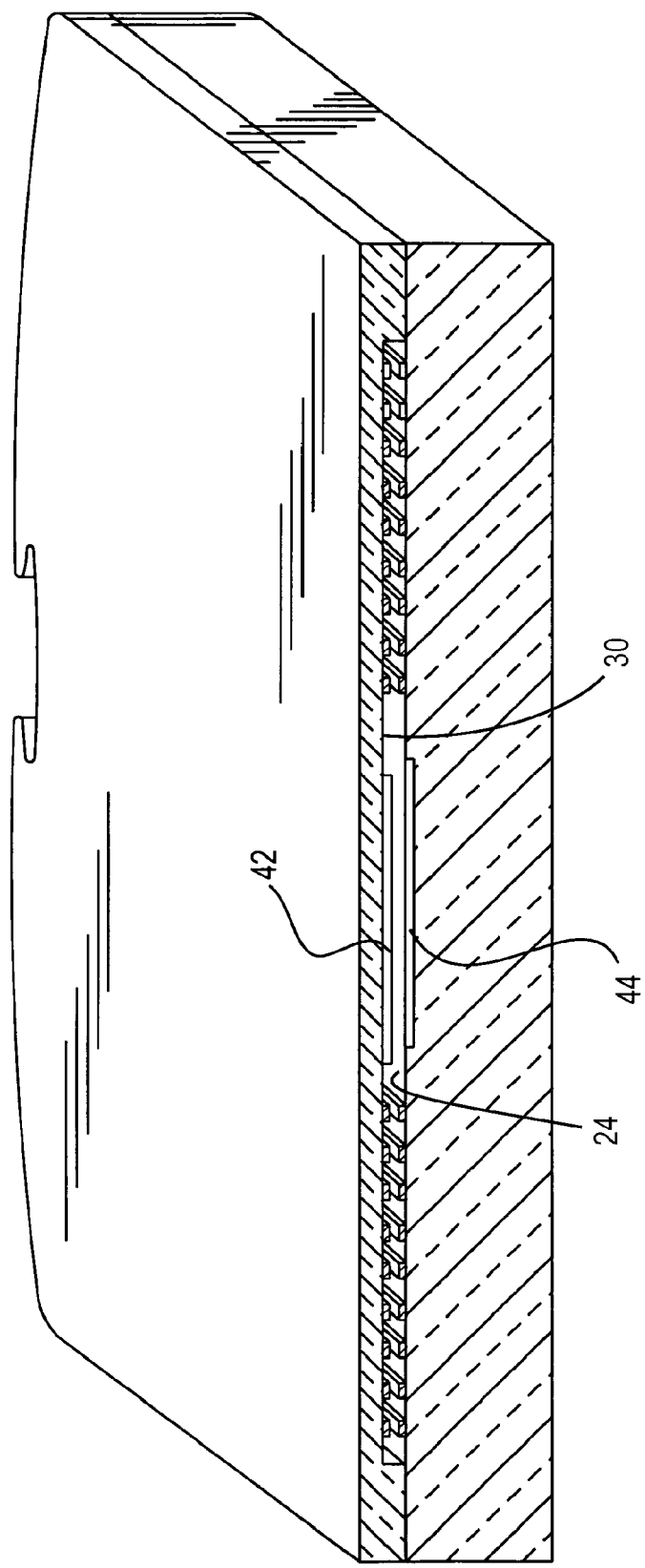
FIG. 5 is an oblique, cross-sectional view of the embodiment of the invention shown in FIG. 3.

In similar fashion, FIG. 5 is a slightly oblique cross-section across its width of the embodiment of the invention shown in FIG. 3. The primary difference between FIGS. 4 and 5 is the presence of upper capacitor plate 42 and lower capacitor plate 44 on surfaces 24 and 30, respectively. In the embodiment of FIG. 4, the spiral coil 4 itself acts as the capacitive element of the LC circuit that describes the operation of the sensor.

Figure 6:
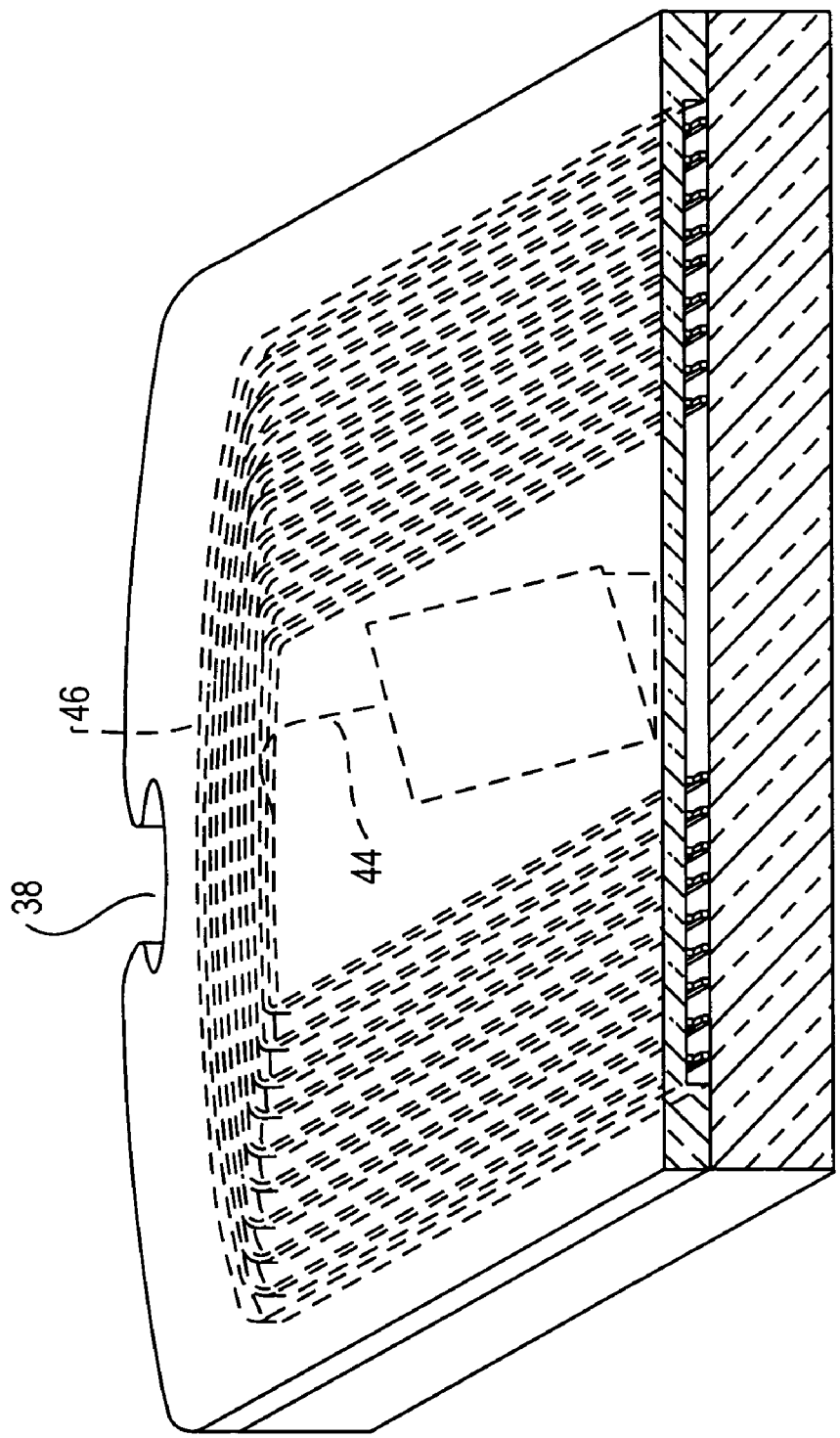
FIG. 6 is a exposed cross-sectional view of the embodiment of the invention shown in FIG. 5.

FIG. 6 is a variation of FIG. 5 where the outline of upper substrate 22 is shown but the details of lower substrate 20 can be seen more clearly, including individual coils of inductor coil 26. A wire 46 connects lower capacitor plate 44 to induction coil 26.

The size of the sensors of the invention will vary according to factors such as the intended application, the delivery system, etc. The oval sensors are intended to be from about 0.5 in. to about 1 in. in length and from about 0.1 in. to about 0.5 in. in width, with a thickness of from about 0.05 in. to about 0.30 in.

As shown in FIGS. 4 and 5, upper substrate 22 can be significantly thinner than lower substrate 20. By way of example, upper substrate 22 may be from about 100 to about 300 microns thick, whereas lower substrate 20 may be from about 500 to about 1500 microns thick. In an alternate embodiment of the invention, both substrates may be of the same thickness ranging from about 100 to about 1000 microns.

Figure 7:
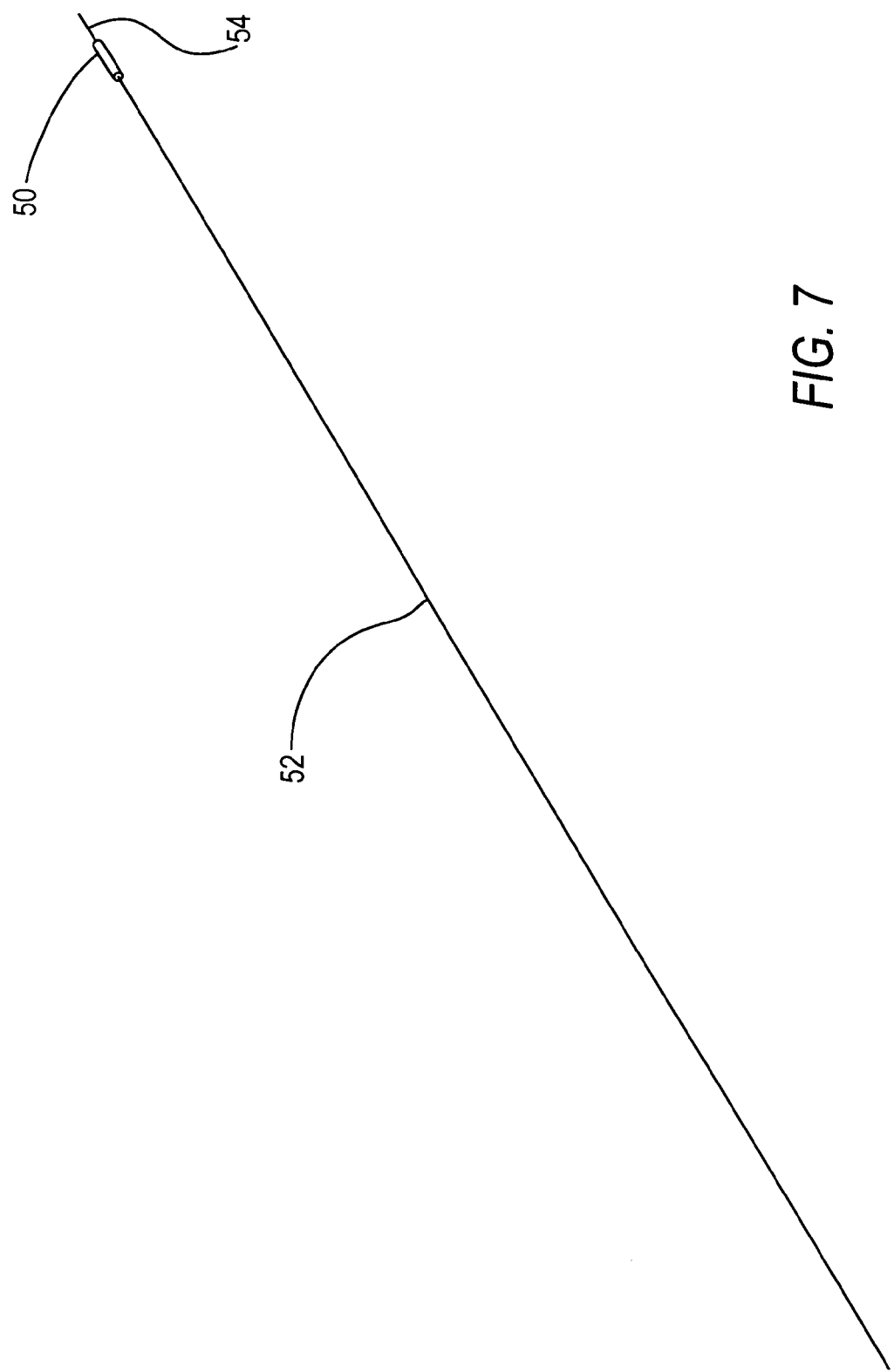
FIG. 7 shows part of the sensor tethering system.

In the embodiment of the invention shown in FIG. 7, a sensor 50 is attached to a hollow tube 52 that has a flexible tip 54.

Figure 8:
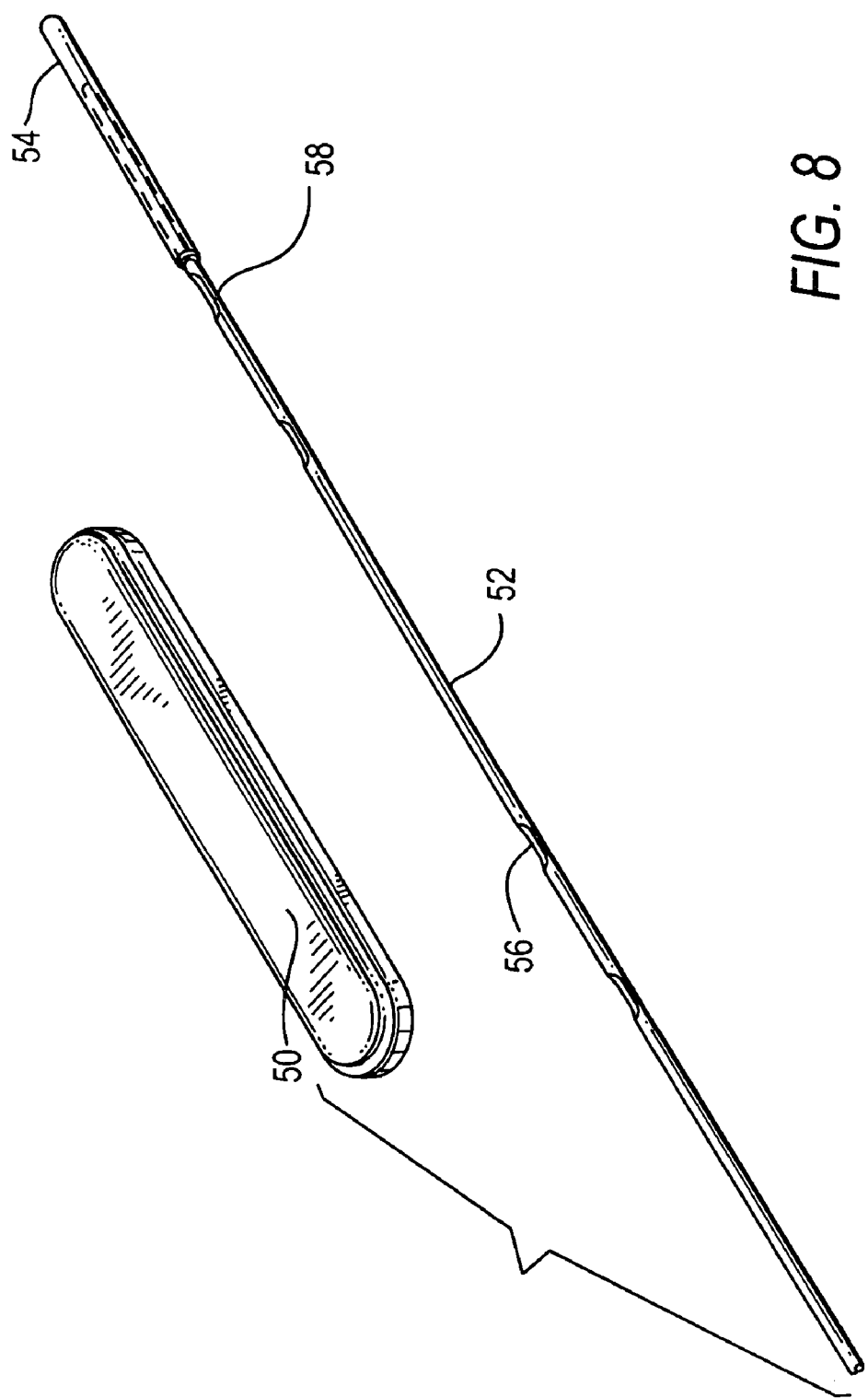
FIG. 8 shows the further details of the tethering system.

FIG. 8 shows the sensor 50 and specific features of the tethering system, namely proximal holes 56 and distal holes 58 disposed in a hollow tube 52.

Figure 9:
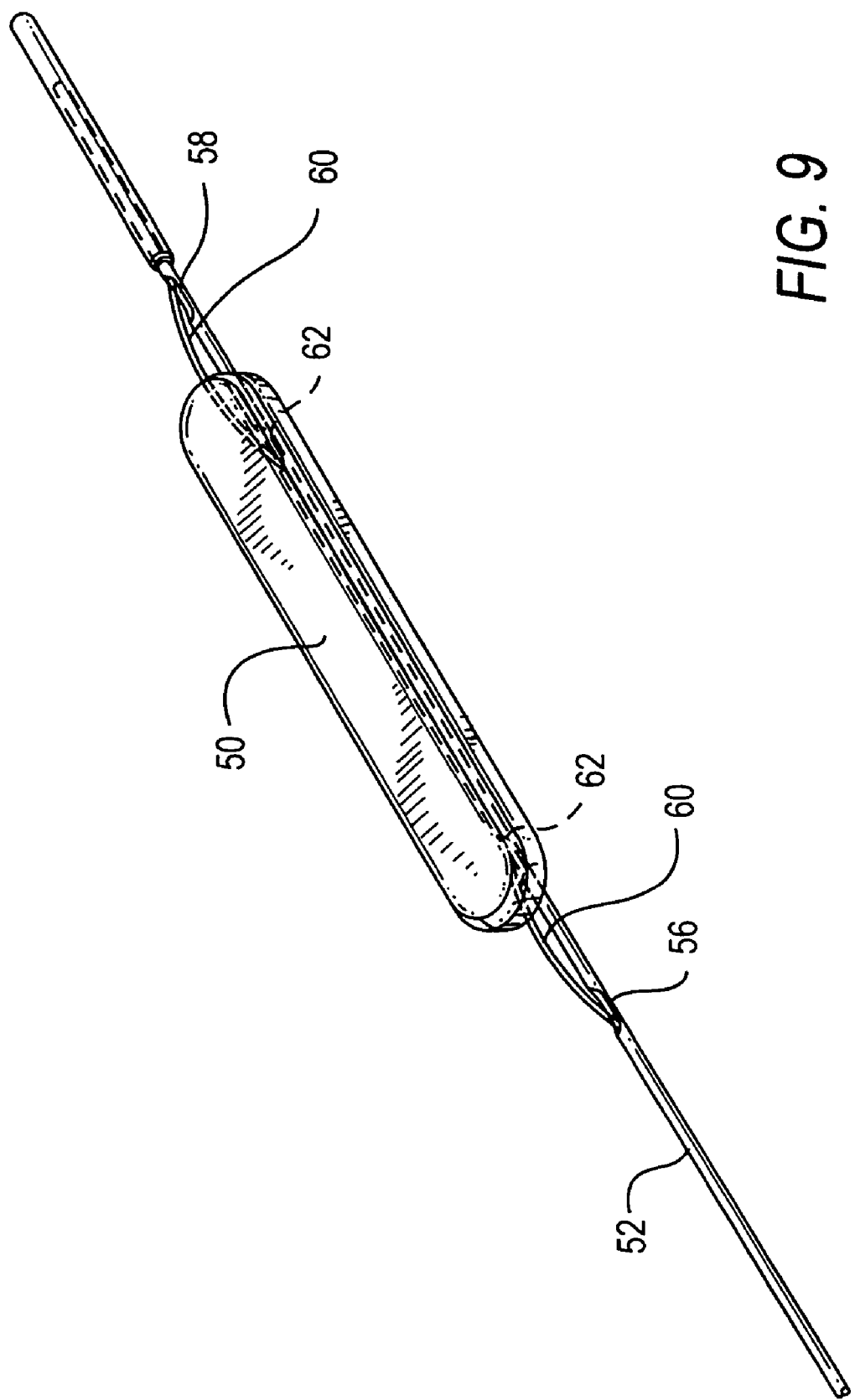

FIG. 9 shows a tether wire 60 that is attached to sensor 50 at sensor holes 62 and hollow tube holes 56 and 58, and a tether wire 60 is positioned slidably within a hollow tube 52.

Figure 10:
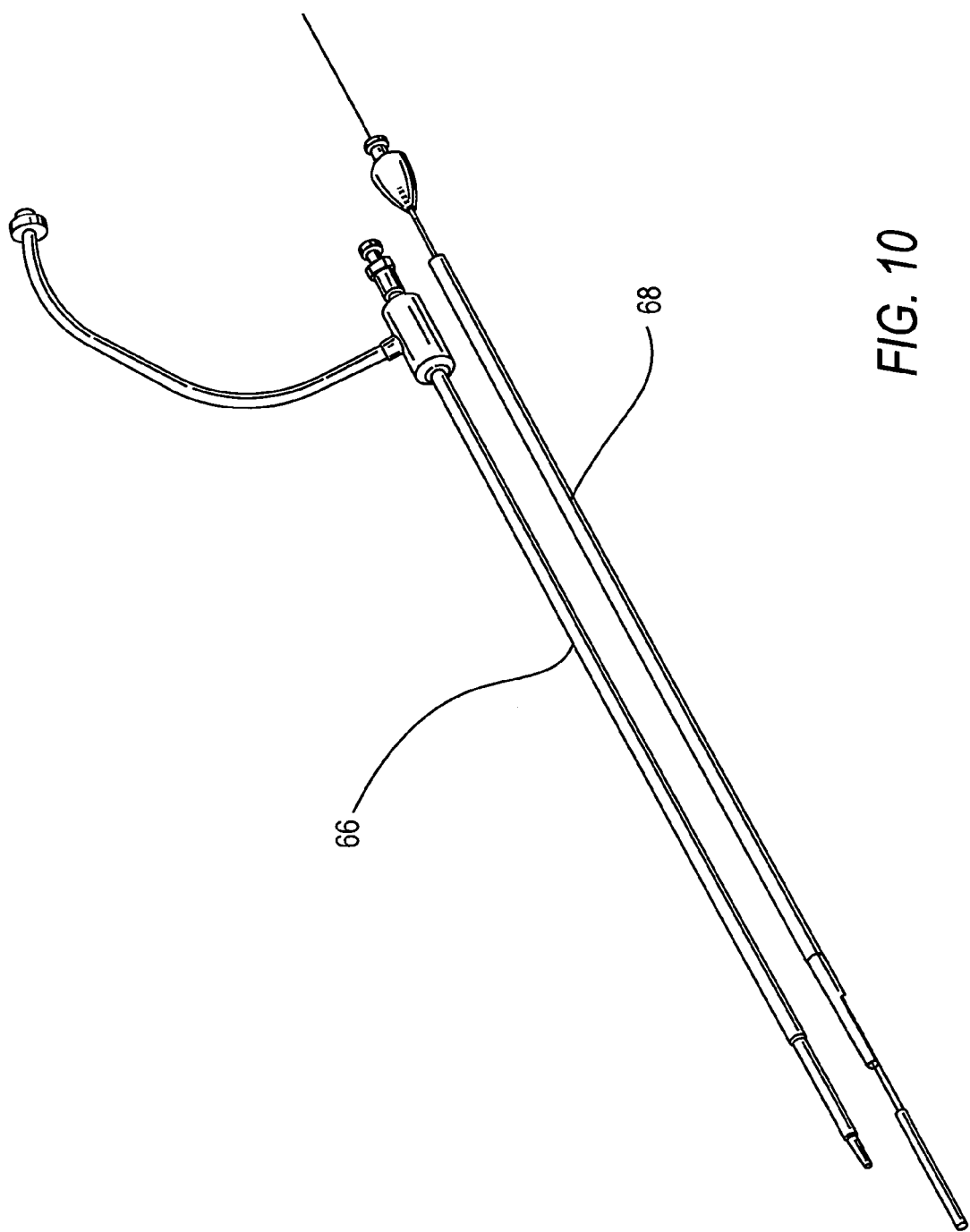

A better appreciation of certain aspects of the invention, especially of a delivery system, can be obtained from FIG. 10 which shows a vessel introducer 66 and the delivery system 68.

Further details of the delivery system are shown in FIG. 11. A double lumen tube 70 has one channel that accepts a guidewire 72 and a second channel that accepts the sensor tether wire. The guidewire 72 can be advanced through hub 74. A rigid delivery capsule 78 is disposed at the far end of the delivery catheter and flexible tip 80 is connected to the catheter via a hollow tube 81 extending through the delivery capsule 78. A sensor 82 is positioned inside a slot in the delivery capsule 78 proximal to flexible tip 80.

FIG. 12 shows a lateral, cross-sectional view of this arrangement where the sensor 82 is inside the slot of delivery capsule 78 and the flexible tip 84 of the tether wire is disposed between the end of delivery capsule 78 and flexible tip 80.

Figure 13:
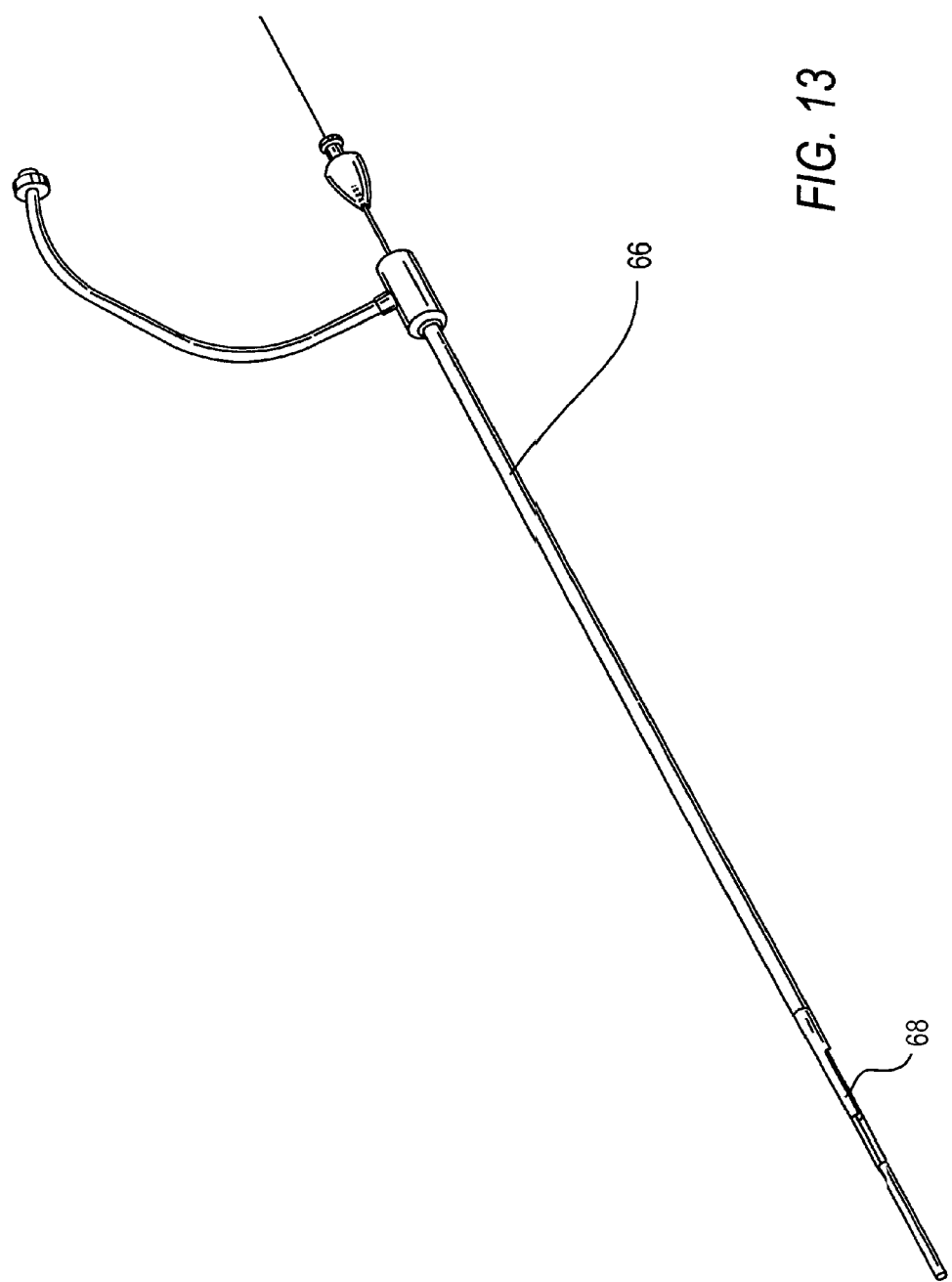

FIG. 13 shows delivery catheter 68 loaded into the previously placed vessel introducer 66 prior to introduction of the sensor into the body.

FIG. 14 shows that the sensor 82 on tether tube 52 has been advanced out of delivery capsule 78 and the delivery catheter has been removed.

In FIG. 15, the tether wire has been retracted into the hollow tether tube, releasing the sensor. The tether wire, tether tube and vessel introducer 66 are then all removed.

The pressure sensor of the invention can be manufactured using Micro-machining techniques that were developed for the integrated circuit industry. An example of this type of sensor features an inductive-capacitive (LC) resonant circuit with a variable capacitor, as is described in Allen et al., U.S. Pat. Nos. 6,111,520 and 6,278,379, all of which are incorporated herein by reference. The sensor contains two types of passive electrical components, namely, an inductor and a capacitor. The sensor is constructed so that the fluid pressure at the sensor's surface changes the distance between the capacitor's substantially parallel plates and causes a variation of the sensor's capacitance.

In a preferred embodiment the sensor of the invention is constructed through a series of steps that use standard MEMS manufacturing techniques.

Figure 16:
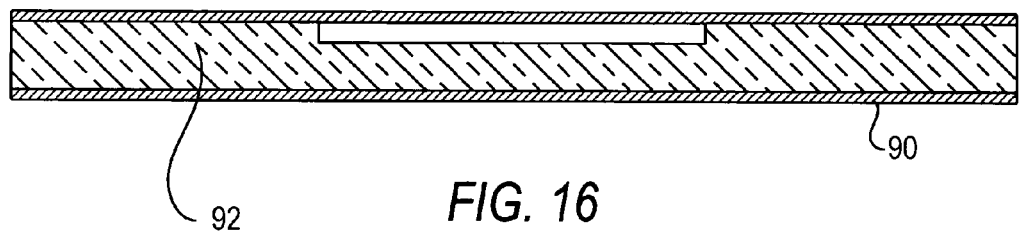
FIGS. 16 to 26 show details of the manufacturing process used to fabricate the invention.

FIG. 16 shows the first step of this process in which a thin layer of metal (Protective mask) 90 is deposited onto the top and bottom surface of a fused silica substrate 92 (alternative materials would be glass, quartz, silicon or ceramic). Substrate diameters can range from about 3 to about 6 in. Substrate thickness can range from about 100 to about 1500 microns. A pattern mask is then created on one side of the substrate to define the location of cavities that need to be etched into the surface.

Figure 17:
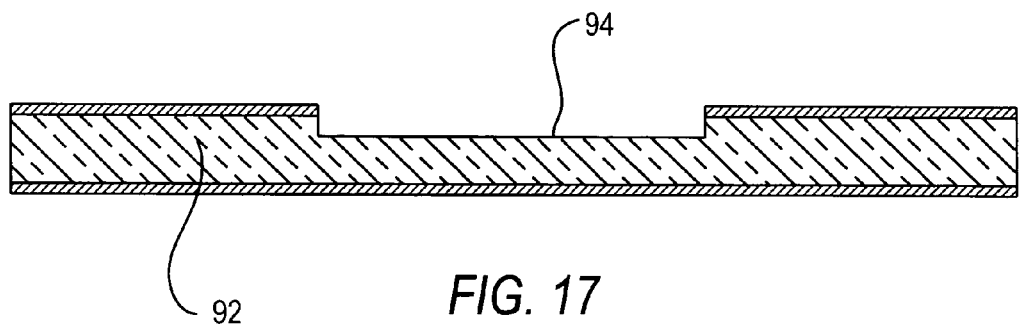
Figure 18:
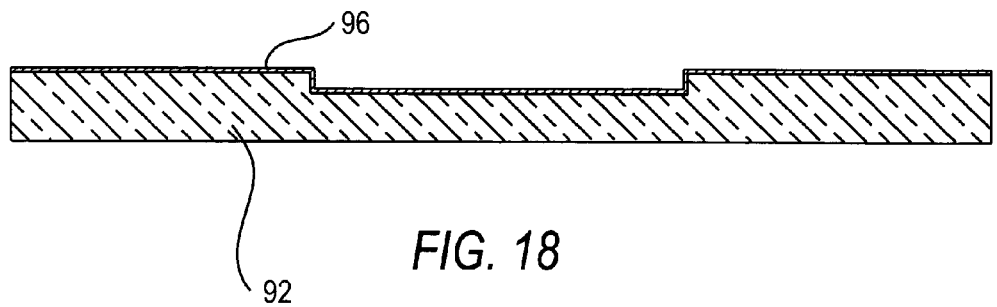

FIG. 17 shows trenches or cavities 94 are etched into one surface of the substrate 92 to depths ranging from about 20 to about 200 microns. This etching is accomplished using any combination of standard wet and dry etching techniques (acid etch, plasma etch, reactive ion etching) that are well known in the MEMS industry. The protective metal mask is removed using standard metal etching techniques In FIG. 18, a thin metal seed layer 96 (typically chromium) is deposited on the etched side of the substrate using standard metal deposition techniques such as sputtering, plating or metal evaporation.

Figure 19:
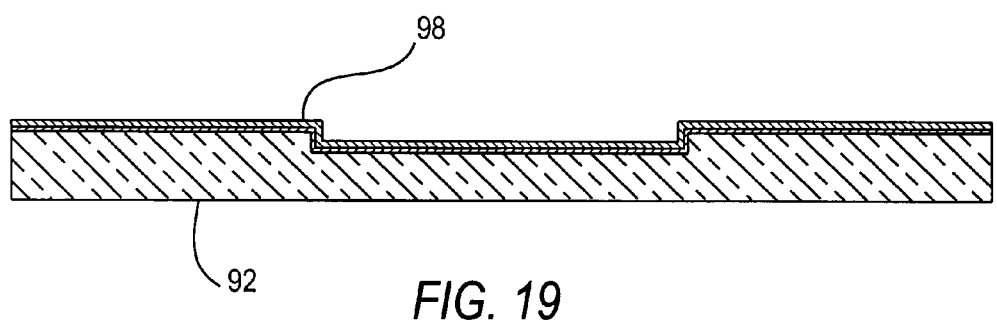

In FIG. 19 a layer of photo-resistive material 98 is applied to the etched surface of the substrate using standard spin coating procedures.

Figure 20:
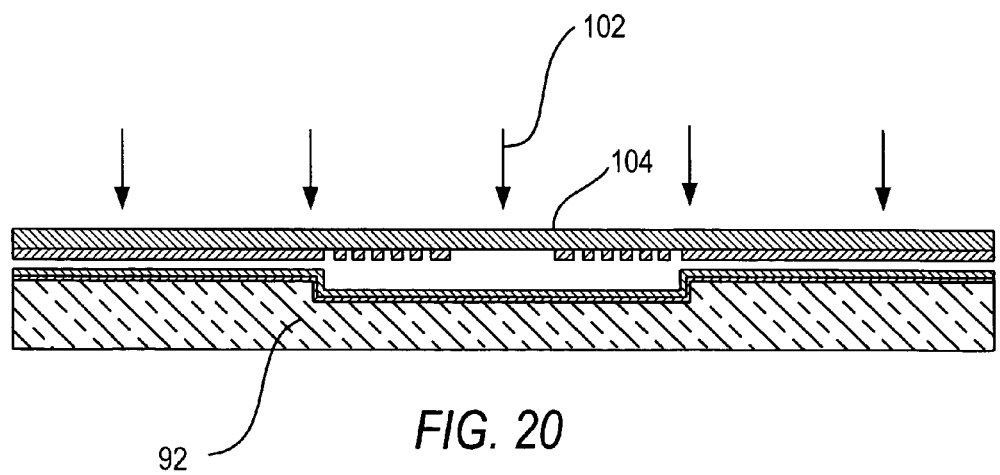

FIG. 20 shows that a mask aligner and UV light 102 is used in a photolithographic processes to transfer a pattern from a mask 104 to the photoresist coating on the substrate.

Figure 21:
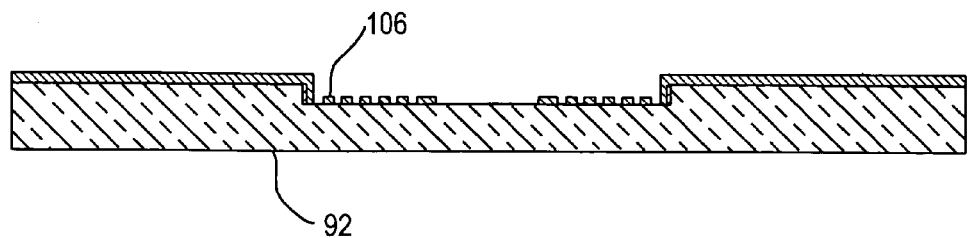

In FIG. 21, the non-masked portions of the Photoresist are removed chemically creating a mold 106 of the desired coil pattern.

Figure 22:
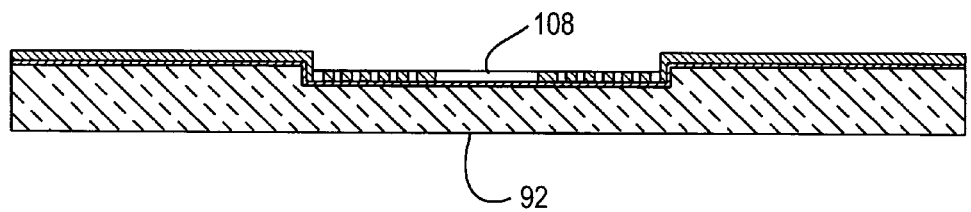

FIG. 22 shows copper 108 electroplated into the mold to the desired height, typically from about 5 to about 35 microns.

Figure 23:
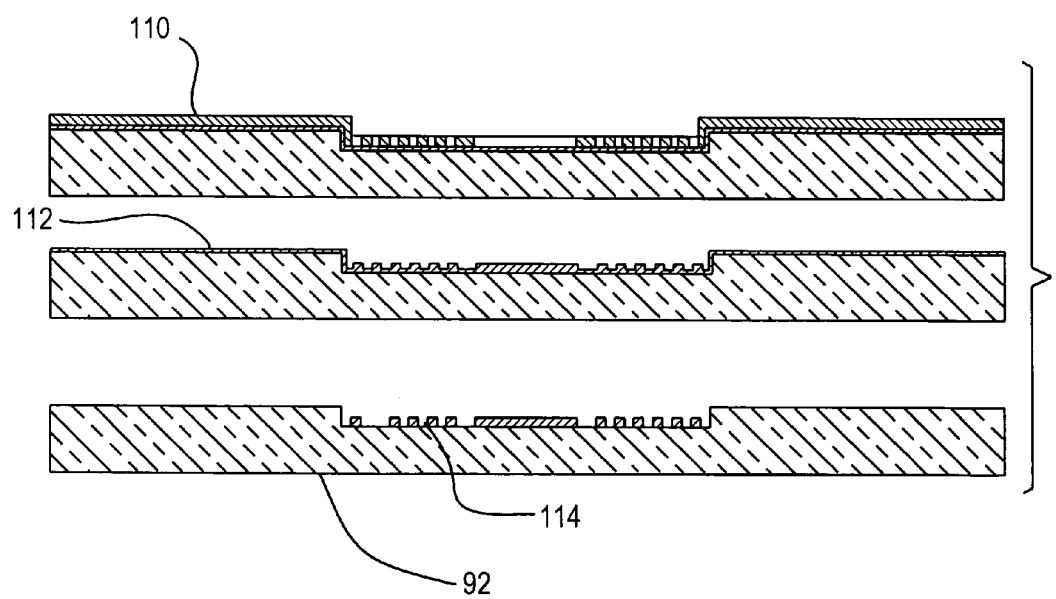

In FIG. 23, the Photoresist 110 and seed layer 112 are etched away leaving the plated copper coils 114.

This process is then repeated with a second substrate.

Figure 24:
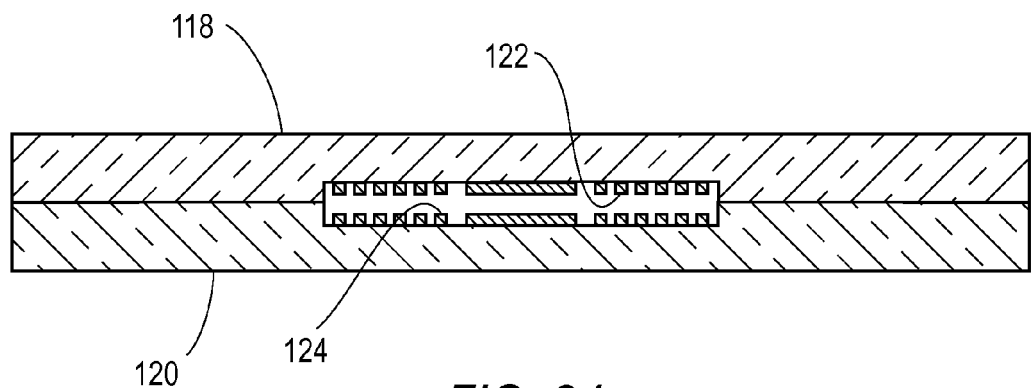

In FIG. 24, the two processed substrates 118 and 120 are aligned such that the cavities 122 and 124 with plated coils are precisely orientated in over one another and temporarily bonded to each other.

Figure 25:
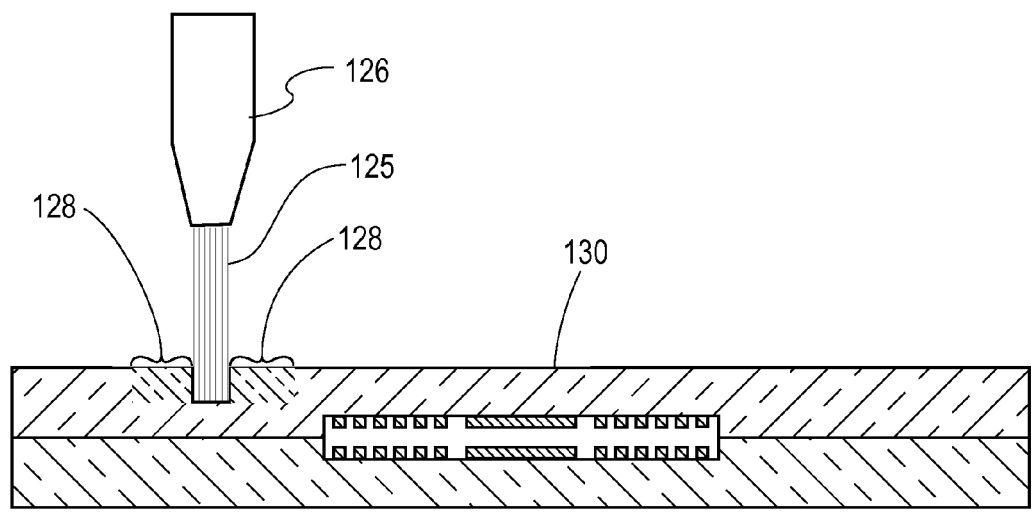
Figure 26:
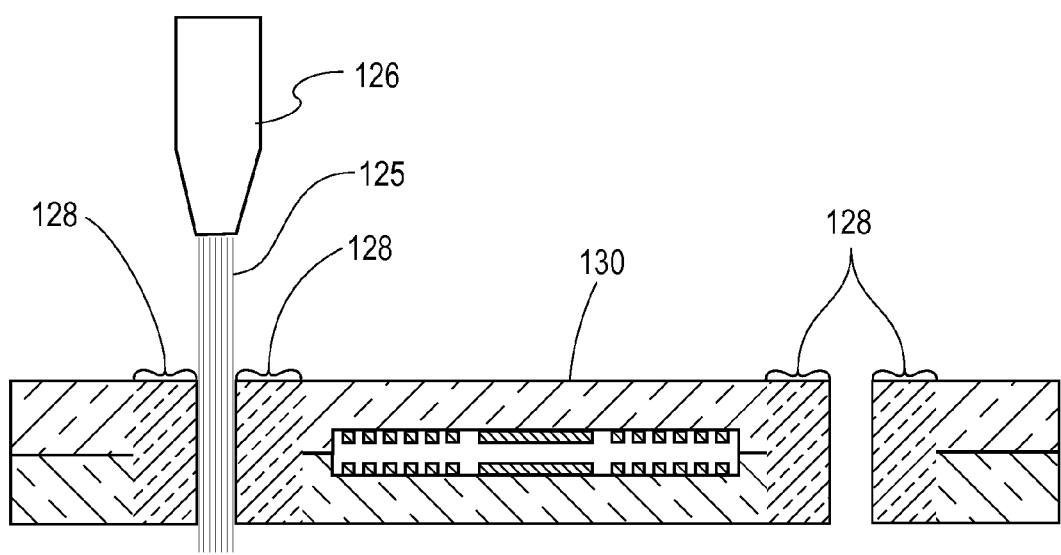

FIGS. 25 and 26 show that by using a beam 125 from a CO2 laser 126 (or other appropriate laser type), the individual sensors 130 are cut from the glass substrate. FIG. 25 shows an early stage in the cutting process where the laser beam 125 has only just begun heating up the surrounding material. FIG. 26 shows a later stage in the process where one side has already been completely cut and sealed, and the laser beam is in the process of cutting and sealing the other side. The laser cutting process results in a permanent, hermetic seal between the two glass substrates. The laser energy is confined to a precise heat effect zone 128 in which the hermetic seal is created.

Figure 27:
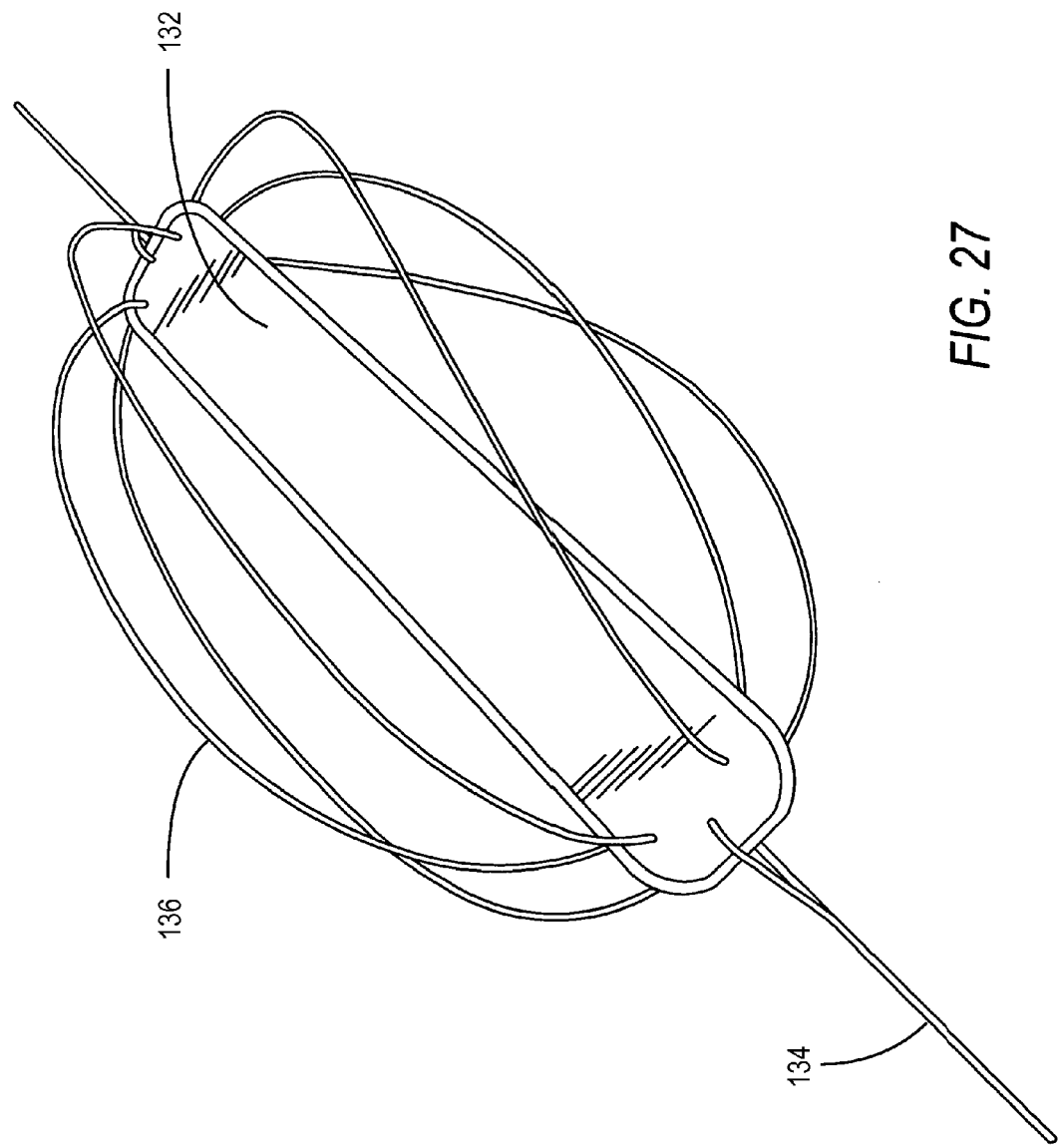
FIG. 27 represents an additional embodiment of the invention.

FIG. 27 represents an embodiment of the invention wherein a sensor 132 attached to a delivery catheter 134 has a stabilizer or basket 136. The stabilizer can be any appropriate device or structure that can be fixedly attached to a sensor of the invention to assist the sensor in maintaining position, location, and/or orientation after the sensor is delivered to an intended site. The stabilizer can comprise any appropriate physiologically acceptable rigid or slightly flexible material, such as stainless steel, nitinol, or a radiopaque metal or alloy.

This sensor design provides many important benefits to sensor performance. The hermetic seal created during the laser cutting process, coupled with the design feature that the conductor lines of the sensor are sealed within the hermetic cavity, allows the sensor to remain stable and drift free during long time exposures to body fluids. In the past, this has been a significant issue to the development of sensors designed for use in the human body. The manufacturing methodology described above allows many variations of sensor geometry and electrical properties. By varying the width of the coils, the number of turns and the gap between the upper and lower coils the resonant frequency that the device operates at and the pressure sensitivity (i.e., the change in frequency as a result of membrane deflection) can be optimized for different applications. In general, the design allows for a very small gap between the coils (typically between about 3 and about 35 microns) that in turn provides a high degree of sensitivity while requiring only a minute movement of the coils to sense pressure changes. This is important for long term durability, where large membrane deflection could result in mechanical fatigue of the pressure sensing element.

The thickness of the sensor used can also be varied to alter mechanical properties. Thicker substrates are more durable for manufacturing. Thinner substrates allow for creating of thin pressure sensitive membranes for added sensitivity. In order to optimize both properties the sensors may be manufactured using substrates of different thicknesses. For example, one side of the sensor may be constructed from a substrate of approximate thickness of 200 microns. This substrate is manufactured using the steps outlined above. Following etching, the thickness of the pressure sensitive membrane (i.e., the bottom of the etched trench) is in the range of from about 85 to about 120 microns.

The matching substrate is from about 500 to about 1000 microns thick. In this substrate, the trench etching step is eliminated and the coils are plated directly onto the flat surface of the substrate extending above the substrate surface a height of from about 20 to about 40 microns. When aligned and bonded, the appropriate gap between the top and bottom coils is created to allow operation preferably in a frequency range of from 30 to 45 MHz and have sensitivity preferably in the range of from 5 to 15 kHz per millimeter of mercury. Due to the presence of the from about 500 to about 1000 micron thick substrate, this sensor will have added durability for endovascular delivery and for use within the human body.

The sensor exhibits the electrical characteristics associated with a standard LC circuit. An LC circuit can be described as a closed loop with two major elements, a capacitor and an inductor. If a current is induced in the LC loop, the energy in the circuit is shared back and forth between the inductor and capacitor. The result is an energy oscillation that will vary at a specific frequency. This is termed the resonant frequency of the circuit and it can be easily calculated as its value is dependent on the circuit's inductance and capacitance. Therefore, a change in capacitance will cause the frequency to shift higher or lower depending upon the change in the value of capacitance.

As noted above, the capacitor in the assembled pressure sensor consists of the two circular conductive segments separated by an air gap. If a pressure force is exerted on these segments it will act to move the two conductive segments closer together. This will have the effect of reducing the air gap between them which will consequently change the capacitance of the circuit. The result will be a shift in the circuit's resonant frequency that will be in direct proportion to the force applied to the sensor's surface.

Because of the presence of the inductor, it is possible to electromagnetically couple to the sensor and induce a current in the circuit. This allows for wireless communication with the sensor and the ability to operate it without the need for an internal source of energy such as a battery. Thus, if the sensor is located within the sac of an aortic aneurysm, it will be possible to determine the pressure within the sac in a simple, non-invasive procedure by remotely interrogating the sensor, recording the resonant frequency and converting this value to a pressure measurement. The readout device generates electromagnetic energy that penetrates through the body's tissues to the sensor's implanted location. The sensor's electrical components absorb a fraction of the electromagnetic energy that is generated by the readout device via inductive coupling. This coupling induces a current in the sensor's circuit that oscillates at the same frequency as the applied electromagnetic energy. Due to the nature of the sensor's electromechanical system there exists a frequency of alternating current at which the absorption of energy from the readout device is at a maximum. This frequency is a function of the capacitance of the device. Therefore, if the sensor's capacitance changes, so will the optimal frequency at which it absorbs energy from the readout device. Since the sensor's capacitance is mechanically linked to the fluid pressure at the sensor's surface, a measurement of this frequency by the readout device gives a relative measurement of the fluid pressure. If calibration of the device is performed, then an absolute measurement of pressure can be made. See, for example, the extensive discussion in the Allen et al. patent, again incorporated herein by reference, as well as Gershenfeld et al., U.S. Pat. No. 6,025,725, incorporated herein by reference. Alternative readout schemes, such as phase-correlation approaches to detect the resonant frequency of the sensor, may also be employed.

The pressure sensor is made of completely passive components having no active circuitry or power sources such as batteries. The pressure sensor is completely self-contained having no leads to connect to an external circuit or power source. Furthermore, these same manufacturing techniques can be used to add additional sensing capabilities, such as the ability to measure temperature by the addition of a resistor to the basic LC circuit or by utilizing changes in the back pressure of gas intentionally sealed within the hermetic pressure reference to change the diaphragm position and therefore the capacitance of the LC circuit.

It is within the scope of the invention that the frequency response to the sensor will be in the range of from about 1 to about 200 MHz, preferably from about 1 to about 100 MHz, and more preferably from about 2 to about 90 MHz, and even more preferably from about 30 to about 45 MHz, with a Q factor of from about 5 to about 150, optimally from about 5 to about 80, preferably from about 40 to about 100, more preferably from about 50 to about 90.

In a further embodiment of the invention there is no direct conductor-based electrical connection between the two sides of the LC circuit. Referring again to the sensor described in the Allen et al. patents, the device is constructed using multiple layers upon lie the necessary circuit elements. Disposed on the top and bottom layer are metal patterns constructed using micro-machining techniques which define a top and bottom conductor and a spiral inductor coil. To provide for an electrical contact between the top and bottom layers small vias or holes are cut through the middle layers. When the layers are assembled, a metal paste is forced into the small vias to create direct electrical connections or conduits. However, experimentation has shown that due to additional capacitance that is created between the top and bottom inductor coils, a vialess operational LC circuit can be created. This absence of via holes represents a significant improvement to the sensor in that it simplifies the manufacturing process and, more importantly, significantly increases the durability of the sensor making it more appropriate for use inside the human body.

Further, the invention is not limited to the implantation of a single sensor. Multiple pressure sensors may be introduced into the aneurysm space, each being positioned at different locations. In this situation, each sensor may be designed with a unique signature (obtained by changing the resonant frequency of the sensor), so that the pressure measurement derived from one sensor can be localized to its specific position within the aneurysm.

A significant design factor that relates to the performance of the sensor and the operation of the system is the Quality factor (Q) associated with the sensor. The value of Q is one of the key determinates as to how far from the sensor the external read-out electronics can be located while still maintaining effective communication. Q is defined as a measure of the energy stored by the circuit divided by the energy dissipated by the circuit. Thus, the lower the loss of energy, the higher the Q.

Additional increases in Q can be achieved by removing the central capacitive plate and using capacitive coupling between the copper coils to act as the capacitor element.

In operation, energy transmitted from the external read-out electronics will be stored in the LC circuit of the sensor. This stored energy will induce a current in the LC loop which will cause the energy to be shared back and forth between the inductor and capacitor. The result is an oscillation that will vary at the resonant frequency of the LC circuit. A portion of this ocscillating energy is then coupled back to the receiving antenna of the read-out electronics. In high Q sensors, most of the stored energy is available for transmission back to the electronics, which allows the distance between the sensor and the receiving antenna to be increased. Since the transmitted energy will decay exponentially as it travels away from the sensor, the lower the energy available to be transmitted, the faster it will decay below a signal strength that can be detected by the receiving antenna and the closer the sensor needs to be situated relative to the receiving electronics. In general then, the lower the Q, the greater the energy loss and the shorter the distance between sensor and receiving antenna required for sensor detection.

The Q of the sensor will be dependent on multiple factors such as the shape, size, diameter, number of turns, spacing between turns and cross-sectional area of the inductor component. In addition, Q will be greatly affected by the materials used to construct the sensors. Specifically, materials with low loss tangents will provide the sensor with higher Q factors.

The implantable sensor ascending to the invention is preferably constructed of various glasses or ceramics including but not limited to fused silica, quartz, pyrex and sintered zirconia, that provide the required biocompatibility, hermeticity and processing capabilities. Preferably the materials result in a high Q factor. These materials are considered dielectrics, that is, they are poor conductors of electricity, but are efficient supporters of electrostatic or electroquasiatatic fields. An important property of dielectric materials is their ability to support such fields while dissipating minimal energy. The lower the dielectric loss (the proportion of energy lost), the more effective the dielectric material in maintaining high Q. For a lossy dielectric material, the loss is described by the property termed "loss tangent." A large loss tangent reflects a high degree of dielectric loss.

With regard to operation within the human body, there is a second important issue related to Q, namely, that blood and body fluids are conductive mediums and are thus particularly lossy. The consequence of this fact is that when a sensor is immersed in a conductive fluid, energy from the sensor will dissipate, substantially lowering the Q and reducing the sensor-to-electronics distance. For example, the sensors described above were immersed in saline (0.9% salt solution), and the measured Q decreased to approximately 10. It has been found that such loss can be minimized by further separation of the sensor from the conductive liquid. This can be accomplished, for example, by encapsulating the sensor in a suitable low-loss-tangent dielectric material. However, potential encapsulation material must have the flexibility and biocompatibility characteristics of the sensor material and also be sufficiently compliant to allow transmission of fluid pressure to the pressure sensitive diaphragm. A preferred material for this application is polydimethylsiloxane (silicone).

As an example, a thin (i.e., 200 micron) coating of silicone was applied to the sensor detailed above. This coating provided sufficient insulation to maintain the Q at 50 in a conductive medium. Equally important, despite the presence of the silicone, adequate sensitivity to pressure changes was maintained and the sensor retained sufficient flexibility to be folded for endovascular delivery. One additional benefit of the silicone encapsulation material is that it can be optionally loaded with a low percentage (i.e., 10-20%) of radio-opaque material (e.g., barium sulfate) to provide visibility when examined using fluoroscopic x-ray equipment. This added barium sulfate will not affect the mechanical and electrical properties of the silicone.

As described above, it is desirable to increase the Q factor of a sensor, and the Q factor can be increased by suitable selection of sensor materials or a coating, or both. Preferably both are used, because the resulting high Q factor of a sensor prepared in this fashion is especially suitable for the applications described.

When introduced into the sac of an abdominal aorta, the pressure sensor can provide pressure related data by use of an external measuring device. As disclosed in the Allen et al. patents, several different excitation systems can be used. The readout device generates electromagnetic energy that can penetrate through the body's tissues to the sensor's implanted location. The sensor's electrical components can absorb a fraction of the electromagnetic energy that is generated by the readout device via inductive coupling. This coupling will induce a current in the sensor's circuit that will oscillate at the same frequency as the applied electromagnetic energy. Due to the nature of the sensor's electromechanical system there will exist a frequency of alternating current at which the absorption of energy from the readout device is at a minimum. This frequency is a function of the capacitance of the device. Therefore, if the sensor's capacitance changes so will the frequency at which it minimally absorbs energy from the readout device. Since the sensor's capacitance is mechanically linked to the fluid pressure at the sensor's surface, a measurement of this frequency by the readout device can give a relative measurement of the fluid pressure. If calibration of the device is performed then an absolute measurement of pressure can be made.

Figure 28:
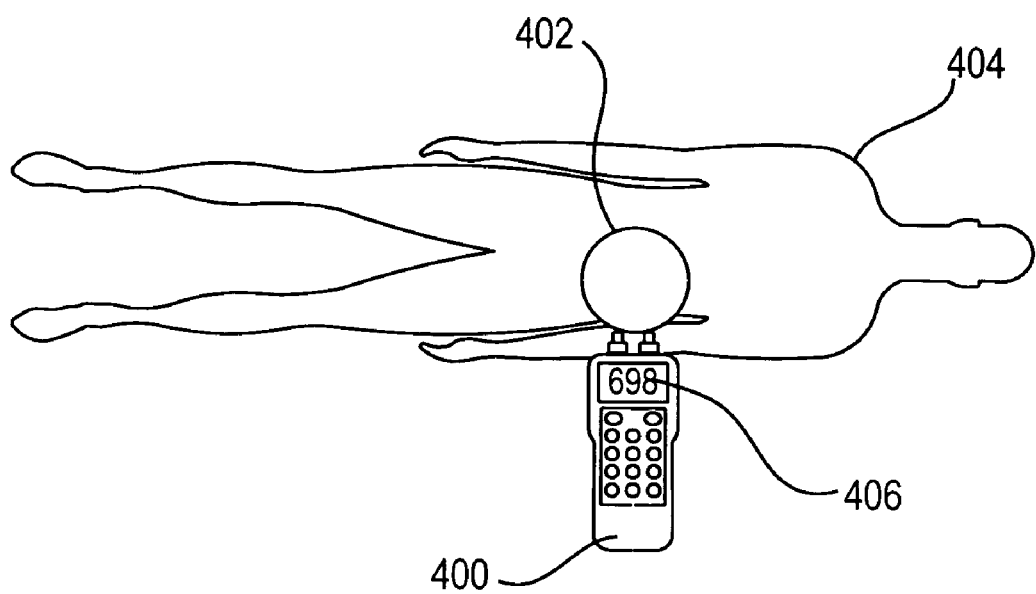
FIG. 28 is a schematic of a control system.

The circuitry used to measure and display pressure is contained within a simple to operate, portable electronic unit 400, as shown in FIG. 28. This unit 400 also contains the antenna 402 needed to perform the electromagnetic coupling to the sensor. The antenna 402 may be integrated into the housing for the electronics or it may be detachable from the unit 400 so that it can be positioned on the surface of the body 404 in proximity to the implanted sensor and easily moved to optimize the coupling between antenna and sensor. The antenna 402 itself may consist of a simple standard coil configuration or my incorporate ferrous elements to maximize the coupling efficiency. The electronic device 400 would feature an LCD or LED display 406 designed to clearly display the recorded pressure in physiologically relevant units such as mm Hg. In an alternative embodiment, the display 406 may be created by integrating a commercially available hand-held computing device such as a Palm® or micro-PC into the electronic circuitry and using this device's display unit as the visual interface between the equipment and its operator. A further advantage of this approach is that the hand-held computer could be detached from the read-out unit and linked to a standard desktop computer. The information from the device could thus be downloaded into any of several commercially available data acquisition software programs for more detailed analysis or for electronic transfer via hard media or the internet to a remote location.

Accordingly, the present invention provides for an impedance system and method of determining the resonant frequency and bandwidth of a resonant circuit within a particular sensor. The system includes a loop antenna, which is coupled to an impedance analyzer. The impedance analyzer applies a constant voltage signal to the loop antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from transmitting antenna, and, electromagnetically coupling a resonant circuit on a sensor to the transmitting antenna thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies, or a time-gated single frequency is applied to the transmitting antenna for a predetermined period of time, thereby inducing a current in the resonant circuit of the sensor at the resonant frequency. The system then listens for a return signal which is coupled back from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna thereby inducing a current in the sensor circuit, listening for and receiving a return signal radiated from the sensor circuit, and determining the resonant frequency and bandwidth from the return signal.

The present invention also provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The invention further includes an alternative method of measuring pressure in which a non-linear element such as a diode or polyvinylidenedifloride piezo-electric polymer is added to the LC circuit. A diode with a low turn-on voltage such as a Schottky diode can be fabricated using micromachining techniques. The presence of this non-linear element in various configurations within the LC circuit can be used to modulate the incoming signal from the receiving device and produce different harmonics of the original signal. The read-out circuitry can be tuned to receive the particular harmonic frequency that is produced and use this signal to reconstruct the fundamental frequency of the sensor. The advantage of this approach is two-fold; the incoming signal can be transmitted continuously and since the return signal will be at different signals, the return signal can also be received continuously.

The above methods lend themselves to the creation of small and simple to manufacture hand-held electronic devices that can be used without complication.

The preceding specific embodiments are illustrative of the practice of the invention. It is to be understood, however, that other expedients known to those skilled in the art or disclosed herein, may be employed without departing from the spirit of the invention of the scope of the appended claims.

We claim:

1. A method of manufacturing a sensor, comprising the steps of:
    forming a first cavity in a first side of a first substrate, the first cavity having a base;
    forming a first conductive structure on the base of the first cavity;
    forming a second conductive structure on a surface of a second substrate;
    mutually imposing the first and second substrates such that the first and second conductive structures are disposed in opposed, spaced-apart relation; and
    using heat from a laser to bond the first and second substrates together and simultaneously to individualize the sensor, the heat being controlled such that said first and second conductive structures are not damaged thereby.

2. The method of claim 1, wherein the step of using heat from a laser to heat bond the first and second substrates together and simultaneously to individualize the sensor comprises the step of creating a hermetic seal between the first and second substrates.

3. The method of claim 1, wherein the step of forming a first conductive structure further comprises the step of forming a first coil.

4. The method of claim 3, wherein the step of forming a second conductive structure further comprises the step of forming a second coil.

5. The method of claim 1, wherein the step of forming a first conductive structure on the base of the first cavity further comprises forming a first conductive spiral coil on the base of the first cavity; and wherein the step of forming a second conductor on a surface of a second substrate further comprises forming a second conductive spiral coil on the second substrate.

6. The method of claim 1, wherein the step of forming a first conductive structure on the base of the first cavity further comprises forming a first conductive spiral coil and a first conductive plate attached to a terminal end of said first conductive spiral coil on the base of the first cavity; and wherein the step of forming a second conductor on a surface of a second substrate further comprises forming a second conductive spiral coil and a second conductive plate attached to a terminal end of said second conductive spiral coil on the second substrate.

7. The method of claim 1, wherein the step of forming a second conductive structure on a surface of a second substrate comprises the steps of:
    etching a second cavity in a first side of the second substrate, the second cavity having a base; and
    forming the second conductive structure on the base of the second cavity.

8. The method of claim 7, wherein the step of mutually imposing the first and second substrates comprises the step of mutually imposing the first and second substrates such that the first and second cavities communicate to form a hollow space.

9. The method of claim 1, wherein the step of forming a first cavity in a first side of a first substrate comprises the step of forming a first cavity in a first side of a substrate comprised of a material selected from the group consisting of fused silica, glass, quartz, silicon, and ceramic.

10. The method of claim 9, wherein the step of forming a second conductive structure on a surface of a second substrate comprises the step of forming a second conductive structure on a surface of a second substrate comprised of a material selected from the group consisting of fused silica, glass, quartz, silicon, and ceramic.

11. The method of claim 1, wherein the step of forming a first cavity in a first side of a first substrate comprises the steps of:
applying a mask to the first side of the first substrate, the mask exposing portions of the first side of the first substrate therethrough; and
etching away the portions of the first side of the first substrate exposed through the mask to form the first cavity.

12. The method of claim 11, wherein the step of etching away the portions of the first side of the first substrate exposed through the mask to form the first cavity is accomplished by a process selected from the group consisting of chemical etching, acid etching, plasma etching, and reactive ion etching.

13. The method of claim 1, wherein the step of etching a first cavity in a first side of a first substrate comprises the step of etching a first cavity in a first side of a first substrate to a depth of from about 20 to about 200 micrometers.

14. The method of claim 1, wherein the step of forming a first cavity in a first side of a first substrate comprises the step of forming a first cavity in a first side of a first substrate having a thickness of from about 100 to about 1500 microns.

15. The method of claim 1, wherein the step of forming a first conductive structure on the base of the first cavity comprises the steps of:
applying a layer of photo-resistive material to the base of the first cavity;
using ultraviolet light in a photolithographic process to transfer a pattern from a mask to the photo-resistive material on the base of the first cavity;
chemically removing portions of the photo-resistive material to create a mold;
depositing a metal into the mold; and
etching away the photo-resistive material to leave the metal.

16. The method of claim 15, wherein the step of applying a layer of photo-resistive material to the base of the first cavity comprises the steps of:
depositing a seed layer onto the base of the first cavity; and
applying the layer of photo-resistive material onto the seed layer.

17. The method of claim 16, wherein the step of depositing a seed layer onto the base of the first cavity is achieved using a process selected from the group consisting of sputtering, plating, and metal evaporation.

18. The method of claim 15, wherein the step of applying a layer of photo-resistive material to the base of the first cavity is achieved by a spin coating procedure.

19. The method of claim 15, wherein the step of depositing a metal into the mold comprises the step of depositing copper into the mold.

20. The method of claim 15, wherein the step of depositing a metal into the mold comprises the step of depositing a metal into the mold to a height of from about 5 to about 35 microns above the base of the first cavity.

21. The method of claim 1, further comprising applying a silicone rubber coating to the exterior of the sensor.

22. The method of claim 21, wherein the step of applying a silicone rubber coating to the exterior of the sensor further comprises applying silicone coating to a thickness of about 200 microns.

23. The method of claim 1, wherein mutually imposing the first and second substrates further comprises mutually imposing the first and second substrates such that the first and second conductive structures are spaced from about 3 to about 35 micrometers apart.

24. The method of claim 1, wherein the step of etching a first cavity in a first side of a first substrate further comprises creating a pressure sensitive membrane.

25. The method of claim 24, wherein the step of creating a pressure sensitive membrane further comprises etching a first cavity in a first side of a first substrate to such a depth that the substrate at the base of the cavity has a thickness from about 85 to about 120 micrometers.

26. A method of manufacturing a plurality of sensors, comprising the steps of:
forming a plurality of first cavity cavities in a first side of a first substrate, each of said plurality of first cavities having a base;
forming a plurality of first conductive structures, one on the base of the each of said plurality of first cavity cavities;
forming a plurality of second conductive structures on a surface of a second substrate;
mutually imposing the first and second substrates such that the first and second conductive structures are aligned in opposed, spaced-apart relation; and
using heat to bond the first and second substrates together and simultaneously to individualize a plurality of sensors, the heat being controlled such that said plurality of first and second conductive structures are not damaged thereby.

27. The method of claim 26, wherein the step of using heat to heat bond the first and second substrates together and simultaneously to individualize said plurality of sensors comprises the step of creating a hermetic seal between the first and second substrates.

28. The method of claim 26, wherein the step of forming a plurality of second conductive structures on a surface of a second substrate comprises the steps of:
etching a plurality of second cavities in a first side of the second substrate, each of said plurality of second cavities having a base; and
forming said plurality of second conductive structures on the base of each of said plurality of second cavities.

29. The method of claim 28, wherein the step of mutually imposing the first and second substrates comprises the step of mutually imposing the first and second substrates such that said plurality of first and second cavities communicate to form a plurality of hollow spaces, and wherein said step of using heat to bond the first and second substrates together and simultaneously to individualize a plurality of sensors comprises the step of using a laser to heat bond the first and second substrates together such that the hollow space defined by the first and second substrates is hermetically sealed.

30. The method of claim 26, wherein the step of forming a plurality of first cavities in a first side of a first substrate comprises the steps of:
applying a mask to the first side of the first substrate, the mask exposing portions of the first side of the first substrate therethrough; and
etching away the portions of the first side of the first substrate exposed through the mask to form said plurality of first cavities.

31. The method of claim 30, wherein the step of etching away the portions of the first side of the first substrate exposed through the mask is accomplished by a process selected from the group consisting of chemical etching, acid etching, plasma etching, and reactive ion etching.

32. The method of claim 26, wherein the step of forming a plurality of first conductive structures, one on the base of each of said plurality of first cavities comprises the steps of:
- applying a layer of photo-resistive material to the base of each of said plurality of cavities;
- using ultraviolet light in a photolithographic process to transfer a pattern from a mask to the photo-resistive material on the base of each of said plurality of cavities;
- chemically removing portions of the photo-resistive material to create a mold;
- depositing a metal into the mold; and
- etching away the photo-resistive material to leave the metal.

33. The method of claim 32, wherein the step of applying a layer of photo-resistive material to the base of each of said plurality of cavities comprises the steps of:
- depositing a seed layer onto the base of each of said plurality of cavities; and
- applying the layer of photo-resistive material onto the seed layer.

34. The method of claim 33, wherein the step of depositing a seed layer onto the base of each of said plurality of cavities is achieved using a process selected from the group consisting of sputtering, plating, and metal evaporation.

35. The method of claim 32, wherein the step of applying a layer of photo-resistive material to the base of each of said plurality of cavities is achieved by a spin coating procedure.

36. The method of claim 26, further comprising applying a silicone rubber coating to the exterior of each of said individualized sensors.

37. The method of claim 36, wherein the step of applying a silicone rubber coating to the exterior of each of said individualized sensors further comprises applying silicone coating to a thickness of about 200 microns.

38. The method of claim 26, wherein mutually imposing the first and second substrates further comprises mutually imposing the first and second substrates such that they are spaced from about 3 to about 35 micrometers apart.

39. The method of claim 26, wherein the step of etching a plurality of first cavities in a first side of a first substrate further comprises creating a pressure sensitive membrane.

40. The method of claim 39, wherein the step of creating a pressure sensitive membrane further comprises etching a plurality of first cavities in a first side of a first substrate to such a depth that the substrate at the base of each of said plurality of said cavities has a thickness from about 85 to about 120 micrometers.

* * * * *